United States Patent [19]

Janssens et al.

[11] Patent Number: 5,258,380

[45] Date of Patent: *Nov. 2, 1993

[54] (4-PIPERIDINYLMETHYL AND -HETERO)PURINES

[75] Inventors: Frans E. Janssens, Bonheiden; Gaston S. M. Diels, Ravels, both of Belgium

[73] Assignee: Janssen Pharmaceutica N.V., Beerse, Belgium

[*] Notice: The portion of the term of this patent subsequent to Aug. 20, 2008 has been disclaimed.

[21] Appl. No.: 719,273

[22] Filed: Jun. 21, 1991

Related U.S. Application Data

[60] Division of Ser. No. 323,250, Mar. 9, 1989, Pat. No. 5,041,448, which is a continuation of Ser. No. 858,339, May 1, 1986, abandoned.

Foreign Application Priority Data

Jun. 24, 1985 [GB] United Kingdom ............ 8515934

[51] Int. Cl.$^5$ .................. C07D 473/02; A61K 31/52
[52] U.S. Cl. .................. 514/233.2; 514/261; 544/116; 544/277; 544/282
[58] Field of Search .......... 514/261, 258, 233.2; 544/253, 260, 277, 263, 116

[56] References Cited

U.S. PATENT DOCUMENTS

| | | | |
|---|---|---|---|
| 4,064,136 | 12/1977 | Loew et al. | 260/304 |
| 4,086,347 | 4/1978 | Friebe et al. | 424/253 |
| 4,219,559 | 8/1980 | Janssens et al. | 424/267 |
| 4,556,660 | 12/1985 | Janssens et al. | 514/272 |
| 4,634,704 | 1/1987 | Janssens et al. | 514/253 |
| 4,689,330 | 8/1987 | Janssens et al. | 514/321 |
| 4,695,569 | 9/1987 | Janssens et al. | 514/258 |
| 4,695,575 | 9/1987 | Janssens et al. | 514/322 |
| 4,888,426 | 12/1989 | Janssens et al. | 546/118 |
| 4,988,689 | 1/1991 | Janssens et al. | 514/212 |
| 5,041,448 | 8/1991 | Janssens et al. | 514/266 |

Primary Examiner—Nicholas S. Rizzo
Attorney, Agent, or Firm—Charles J. Metz

[57] ABSTRACT

(4-Piperidinylmethyl and -hetero)purines having antihistaminic properties and being useful agents in the treatment of allergic diseases.

6 Claims, No Drawings

(4-PIPERIDINYLMETHYL AND -HETERO)PURINES

CROSS-REFERENCE TO RELATED APPLICATIONS

This application is a divisional of application Ser. No. 323,250, filed Mar. 9, 1989, now U.S. Pat. No. 5,041,448, which was a continuation of application Ser. No. 858,339, filed May 1, 1986, now abandoned.

BACKGROUND OF THE INVENTION

In U.S. Pat. No. 4,219,559 there are described a number of N-heterocyclyl-4-piperidinamines having antihistaminic properties. In European Patent Publication Nos. 0,099,139: 0,145,037 and 0,144,101 there are also described a number of N-heterocyclyl-4-piperidinamines as compounds having antihistaminic and serotoninantagonistic properties.

The compounds of the present invention differ from the prior art compounds essentially by the nature of the 4-piperidinyl substituent which is invariably a purinylmethyl or -hetero group.

DESCRIPTION OF THE PREFERRED EMBODIMENTS

This invention is concerned with novel (4-piperidinylmethyl and -hetero)purines which may structurally be represented by the formula

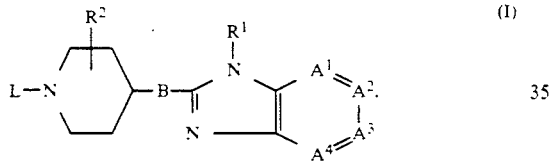

the pharmaceutically acceptable acid addition salts and the possible stereochemically isomeric forms thereof, wherein: $-A^1=A^2-A^3=A^4-$ is a bivalent radical having the formula $$-N=CH-N=CH- \quad (a\text{-}1),$$

or $$-CH=N-CH=N- \quad (a\text{-}2).$$

wherein
one or two hydrogen atoms in said radicals (a-1) or (a-2) may, each independently from each other, be replaced by halo, $C_{1-6}$ alkyl, $C_{1-6}$ alkyloxy, trifluoromethyl or hydroxy;

$R^1$ is a member selected from the group consisting of hydrogen, $C_{1-10}$ alkyl, $C_{3-6}$ cycloalkyl, $Ar^1$ and $C_{1-6}$ alkyl substituted with one or two $Ar^1$ radicals;

$R^2$ is a member selected from the group consisting of hydrogen and $C_{1-6}$ alkyl;

B is $CH_2$, NR, O, S, SO or $SO_2$: said R being a member selected from the group consisting of hydrogen, $C_{1-6}$ alkyl, $C_{3-6}$ cycloalkyl, $(C_{1-6}$ alkyl$)-CO-$, $(C_{1-6}$ alkyloxy$)-CO$ and $Ar^2-C_{1-6}$ alkyl;

L is a member selected from the group consisting of a radical of formula $$L^1-C_rH_{2r}-T-C_sH_{2s}- \quad (b\text{-}1);$$

and a radical of formula

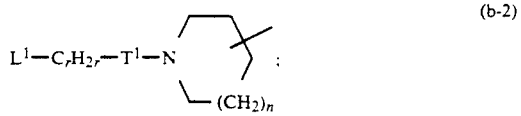

wherein one or two hydrogen atoms in the bivalent radical $-C_sH_{2s}-$ may, each independently from each other, be replaced by halo, hydroxy, mercapto, isothiocyanato, isocyanato, $C_{1-6}$ alkyloxy, $C_{1-6}$ alkylthio, $Ar^1$, $Ar^1O-$, $Ar^1S-$, $Ar^1SO_2-$, or $NHR^3R^5$; and n is 0 or the integer 1 or 2;

r and s are, independently from each other, 0 or an integer of from 1 to 6 inclusive;

T is $-Y-$ or

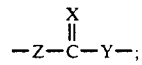

$T^1$ is

or a direct bond: said Y being O, S, $NR^3$ or a direct bond; X being O, S, $CH-NO_2$ or $NR^4$; Z being O, S, $NR^5$ or a direct bond; and said $R^3$ being hydrogen, $C_{1-6}$ alkyl, $Ar^2-C_{1-6}$ alkyl, 2-($C_{1-6}$ alkyloxy)-1,2-dioxoethyl or a radical of formula $-C(=X)-R^6$, $R^6$ being hydrogen, $C_{1-6}$ alkyl, $Ar^2$, $Ar^2-C_{1-6}$ alkyl, $C_{1-6}$ alkyloxy, $Ar^2-C_{1-6}$ alkyloxy, mono- or di($C_{1-6}$ alkyl)amino, $Ar^2$-amino, $Ar^2-C_{1-6}$ alkylamino or $Ar^2-C_{1-6}$ alkyl($C_{1-6}$ alkyl)amino;

said $R^4$ being hydrogen, $C_{1-6}$ alkyl, cyano, nitro, $Ar^2$-sulfonyl, $C_{1-6}$ alkylsulfonyl, $C_{1-6}$ alkylcarbonyl or $Ar^2$-carbonyl; and said $R^5$ being hydrogen or $C_{1-6}$ alkyl;

wherein $L^1$ is a member selected from the group consisting of hydrogen; halo; hydroxy; $C_{1-6}$ alkyloxy; $C_{1-6}$ alkylthio: cyano; mercapto; isocyanato; isothiocyanato; $Ar^1$; $Ar^1$-carbonyl; $Ar^1$-sulfonyl; $C_{1-6}$ alkylsulfonyl; $C_{3-6}$ cycloalkyl being optionally substituted with up to two substituents each independently selected from the group consisting of $C_{1-6}$ alkyl, cyano and $Ar^2$; [10,11-dihydro-5H-dibenzo-[a,d]cyclohepten-5-ylidene]-methyl; Het; and furan substituted with substituted $C_{1-6}$ alkyl; said substituted $C_{1-6}$ alkyl being $C_{1-6}$ alkyl substituted with a member selected from the group consisting of hydroxy, mercapto, $C_{1-6}$ alkyloxy, $C_{1-6}$ alkylthio, amino$C_{1-6}$ alkylthio, $Ar^2$-oxy and a radical of formula

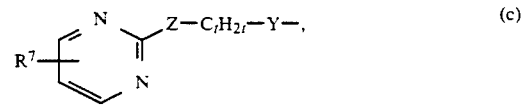

wherein:
t is 0 or an integer of from 1 to 6 inclusive; and
$R^7$ is hydrogen or $C_{1-6}$ alkyl;
provided that: when in said radical of formula (c) t is 0, then Z or Y is a direct bond; and where r is 0, $L^1$ may also be $C_{2-6}$ alkenyl, $Ar^1$—$C_{2-6}$ alkenyl or $C_{1-6}$ alkyl substituted with two $C_{1-6}$ alkyloxy radicals; and where r is 0 and T is $NR^3$, or T is —$N(R^5)$—C(=X)—Y or $T^1$ is —$N(R^5)$—C(=X)—, $L^1$ may also be amino, $C_{1-6}$ alkylamino or $Ar^1$-amino; and where r is 0 and T is —$N(R^5)$—C(=X)—Y or $T^1$ is —$N(R^5)$—C(=X)—, $L^1$ may also be nitro;

said Het being an optionally substituted five- or six-membered heterocyclic ring, being optionally condensed with an optionally substituted five- or six-membered carbocyclic or heterocyclic ring;

provided that:

i) when L is a radical of formula (b-1) wherein $L^1$ is hydrogen and wherein T is —Z—C(=X)—Y— wherein Y is other then a direct bond and Z and X are each independently O or S, then r is not 0; or when L is a radical of formula (b-2) wherein $L^1$ is hydrogen and wherein $T^1$ is —Z—C(=X)— wherein Z and X are each independently or S, then r is not 0;

ii) when L is a radical of formula (b-1) wherein $L^1$ is halo, hydroxy, $C_{1-6}$ alkyloxy, mercapto, $C_{1-6}$ alkylthio, isocyanato, isothiocyanato or Het connected to $C_rH_{2r}$ on a nitrogen atom, and wherein r is 0, then T is a direct bond or a radical —C(=X)—Y—; or when L is a radical of formula (b-2) wherein $L^1$ is halo, hydroxy, $C_{1-6}$ alkyloxy, mercapto, $C_{1-6}$ alkylthio, isocyanato, isothiocyanato or Het connected to $C_rH_{2r}$ on a nitrogen atom, and wherein r is 0, then $T^1$ is a radical —C(=X)—;

iii) when L is a radical of formula (b-1) wherein T is Y, said Y being other than a direct bond, or wherein T is —Z—C(=X)—Y—, wherein Y is other than a direct bond, then s is not 0;

wherein $Ar^1$ is a member selected from the group consisting of phenyl, substituted phenyl, naphthalenyl, thienyl, halothienyl, $C_{1-6}$ alkylthienyl, pyridinyl, mono- and di($C_{1-6}$ alkyloxy)pyridinyl, pyrrolyl, $C_{1-6}$ alkylpyrrolyl, furanyl, furanyl substituted with $C_{1-6}$ alkyl, pyrazinyl, thiazolyl, imidazolyl, $C_{1-6}$ alkylimidazolyl; said substituted phenyl, being phenyl substituted with up to 3 substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, $C_{1-6}$ alkylsulfonyl, $C_{1-6}$ alkylsulfonyl$C_{1-6}$ alkyl, phenyl$C_{1-6}$ alkylsulfonyl, phenylsulfonyl$C_{1-6}$ alkyl, a radical of formula $R^8$—$C_pH_{2p}$—Y—, a radical of formula $R^9$—Z—C(=X)—Y—, and a radical of formula $R^{10}SO_2Y$—; wherein p is an integer of from 1 to 6 inclusive and $R^8$ is a member selected from the group consisting of amino, cyano, phenyl aminocarbonyl, mono- and di($C_{1-6}$ alkyl)aminocarbonyl, $C_{1-6}$ alkyloxycarbonyl, phenyl$C_{1-6}$ alkyloxycarbonyl, 4-morpholinylcarbonyl, 1-piperidinylcarbonyl, 1-pyrrolidinylcarbonyl, and $C_{2-6}$ alkenyl; wherein $R^9$ is member selected from the group consisting of hydrogen, $C_{1-6}$ alkyl and $Ar^2$; provided that, when $R^9$ is hydrogen and Y is other than a direct bond, then Z is not O or S; and wherein $R^{10}$ is $C_{1-6}$ alkyl or $Ar^2$;

wherein $Ar^2$ is a member selected from the group consisting of phenyl, substituted phenyl, thienyl and furanyl, said substituted phenyl being phenyl optionally substituted with up to three substituents each independently selected from the group consisting of halo, hydroxy, nitro, cyano, trifluoromethyl, $C_{1-6}$ alkyl, $C_{1-6}$ alkyloxy, $C_{1-6}$ alkylthio, mercapto, amino, mono- and di($C_{1-6}$ alkyl)amino, carboxyl, $C_{1-6}$ alkyloxycarbonyl and ($C_{1-6}$ alkyl)-CO.

As used in the foregoing definitions the term halo is generic to fluoro, chloro, bromo and iodo; the term "$C_{1-6}$ alkyl" is meant to include straight and branch chained saturated hydrocarbon radicals having from 1 to 6 carbon atoms such as, for example, methyl, ethyl, 1-methylethyl, 1,1-dimethylethyl, propyl, 2-methylpropyl, butyl, pentyl, hexyl and the like; "$C_{1-10}$ alkyl" is meant to include $C_{1-6}$ alkyl radicals, as defined hereinabove, and the higher homologs thereof having from 7 to 10 carbon atoms; the term "$C_{2-6}$ alkenyl" is meant to include straight and branch chained hydrocarbon radicals having from 2 to 6 carbon atoms, such as, for example, 2-propenyl, 2-butenyl, 3-butenyl, 2-pentenyl and the like; the term "$C_{3-6}$ cycloalkyl" is generic to cyclopropyl, cyclobutyl, cyclopentyl and cyclohexyl; and "$C_{1-6}$ alkanediyl" is meant to include bivalent straight or branch chained alkanediyl radicals having from 1 to 6 carbon atoms.

Preferred compounds within the invention are those wherein Het is a five- or six-membered heterocyclic ring containing a number of heteroatoms which varies of from 1 to 4, said heteroatoms being selected from the group consisting of oxygen, sulfur and nitrogen, provided that no more than two oxygens or sulfurs are present, said five or six-membered ring being optionally condensed with a five- or six-membered carbocyclic or heterocyclic ring also containing a number of heteroatoms which varies from 1 to 4, the latter heteroatoms being selected from the group consisting of oxygen, sulfur and nitrogen, provided that no more than 2 oxygens or sulfurs are present, and wherein said Het being a bicyclic ring system may optionally be substituted with up to 6 substituents, or said Het being a monocyclic ring system may optionally be substituted with up to 3 substituents, said substituents of Het being selected from te group consisting of a bivalent radical of formula =X, said =X independently having the same meaning of the previously defined X; halo; isocyanato; isothiocyanato; nitro, cyano, trifluoromethyl; a radical of formula A—Y—, wherein A is hydrogen, $Ar^1$ or $C_{1-6}$ alkyl being optionally substituted with $Ar^1$, $C_{1-6}$ alkyloxy, $Ar^1O$, hydroxy, $C_{1-6}$ alkyloxycarbonyl and Y independently has the same meaning of the previously defined Y; and a radical A—Z—C(=X)—Y—, wherein A is as defined hereinabove and Z, X and Y independently have the same meanings of the previously defined Z, X and Y; provided that (i) when in the radical A—Y— A is hydrogen, then Y is other than a direct bond, or (ii) when in the radical A—Z—C(=X)—Y—A is hydrogen and Y is $NR^3$, O or S, then Z is other than O or S.

Particularly preferred compounds within the invention are those wherein Het is a member selected from the group consisting of i) pyridinyl which is optionally substituted with one or two substituents each independently selected from the group consisting of halo, amino, mono- and di$C_{1-6}$ alkyl amino, $Ar^2$ $C_{1-6}$ alkylamino, nitro, cyano, aminocarbonyl, $C_{1-6}$ alkyl, $C_{1-6}$ alkyloxy, $C_{1-6}$ alkylthio, $C_{1-6}$ alkyloxycarbonyl, hydroxy, $C_{1-6}$ alkylcarbonyloxy, $Ar^2$—$C_{1-6}$ alkyl and carboxyl;

pyridinyloxide optionally substituted with nitro;
quinolinyl which is optionally substituted with C$_{1-6}$ alkyl; pyrimidinyl which is optionally substituted with one or two substituents each independently selected from the group consisting of halo, amino, hydroxy, C$_{1-6}$ alkyl, C$_{1-6}$ alkyloxy, C$_{1-6}$ alkylthio and Ar$^2$—C$_{1-6}$ alkyl;
quinazolinyl which is optionally substituted with hydroxy or C$_{1-6}$ alkyl;
pyridazinyl which is optionally substituted with C$_{1-6}$ alkyl or halo;
quinoxalinyl which is optionally substituted with C$_{1-6}$ alkyl; pyrazinyl which is optionally substituted with halo, amino or C$_{1-6}$ alkyl;
phthalazinyl which is optionally substituted with halo: morfolinyl;
thiomorfolinyl;
piperidinyl;
2,3-dihydro-3-oxo-4$\underline{H}$-benzoxazinyl and 2,3-dihydro-1,4-benzodioxinyl, both being optionally substituted with C$_{1-6}$ alkyl or halo;
dioxanyl being optionally substituted with C$_{1-6}$ alkyl;
2-oxo-2$\underline{H}$-1-benzopyranyl and 4-oxo-4$\underline{H}$-1-benzopyranyl both being optionally substituted with C$_{1-6}$ alkyl;
1,4-dihydro-2,4-dioxo-3(2$\underline{H}$)-pyrimidinyl being optionally substituted with C$_{1-6}$ alkyl; and
4-oxo-2(1$\underline{H}$)-pyrimidinyl;
ii) 5,6-dihydro-4$\underline{H}$-1,3-thiazin-2-yl, thiazolyl, 4,5-dihydrothiazolyl, oxazolyl, imidazolyl, tetrazolyl, 1,3,4-thiadiazolyl, benzimidazolyl, benzothiazolyl, benzoxazolyl, 4,5-dihydro-5-oxo-1$\underline{H}$-tetrazolyl, 2-oxo-3-oxazolidinyl and indolyl whereby each of the Het-radicals of group ii) may optionally be substituted where possible with up to two substituents selected from the group consisting of C$_{1-6}$ alkyl, Ar$^1$, Ar$^1$—C$_{1-6}$ alkyl, benzimidazolylC$_{1-6}$ alkyl, amino, (aminoiminomethyl)amino, mono- and di(C$_{1-6}$ alkyl)amino, Ar$^1$-amino, nitro, C$_{1-6}$ alkyloxycarbonyl and pyrimidinyl;
iii) a radical of formula

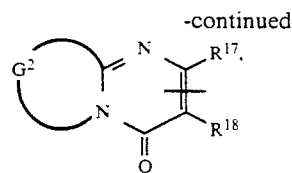

(e-1)

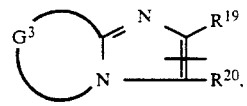

(e-2)

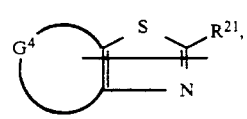

(e-3)

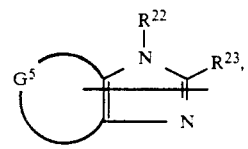

(e-4)

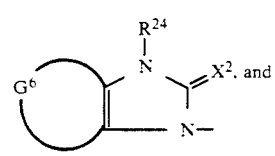

(e-5)

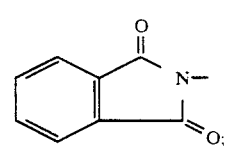

(e-6)

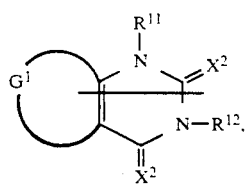

(e-7)

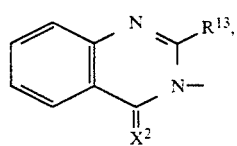

(e-8)

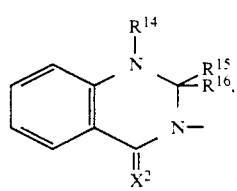

(e-9)

wherein each
X$^2$ is independently O or S;
R$^{11}$, R$^{12}$, R$^{14}$, R$^{22}$ and R$^{24}$ are each independently hydrogen, C$_{1-6}$ alkyl, Ar$^2$—C$_{1-6}$ alkyl, hydroxyC$_{1-6}$ alkyl or C$_{1-6}$ alkyloxycarbonyl;
R$^{13}$, R$^{16}$, R$^{17}$, R$^{18}$, R$^{19}$, R$^{20}$, R$^{21}$ and R$^{23}$ are each independently hydrogen, C$_{1-6}$ alkyl, hydroxy, mercapto, C$_{1-6}$ alkyloxy, C$_{1-6}$ alkylthio, halo and (C$_{1-6}$ alkyloxycarbonyl)C$_{1-6}$ alkyl;
G$^1$ is —CH=CH—CH=CH—, —S—CH=CH— or —N=CH—NH—;
G$^2$ is —CH=CH—CH=CH—, —S—(CH$_2$)$_2$—, —S—(CH$_2$)$_3$—, —(CH$_2$)$_4$— or —S—CH=CH—;
G$^3$ is —CH=CH—CH=CH—, —CH$_2$—NH—(CH$_2$)$_2$—, —S—CH=CH—, —N=CH—CH=CH—, —CH=N—CH=CH—, —CH=CH—N=CH—, —CH=CH—CH=N—, —N=CH—N=CH— or —CH=N—CH=N—;
G$^4$ is —CH$_2$—NH—(CH$_2$)$_2$—, —N=CH—CH=CH— —CH=N—CH=CH—, —CH=CH—N=CH—, —CH=CH—CH=N—, —N=CH—N=CH— or —CH=N—CH=N—;
G$^5$ is —N=CH—CH=CH—, —CH=N—CH=CH—, —CH=CH—N=CH—, —CH=CH—CH=N—, —N=CH—N=CH— or —CH=N—CH=N—;
G$^6$ is —CH=CH—CH=CH—, —N=CH—CH=CH—, —CH=N—CH=CH—, —CH=

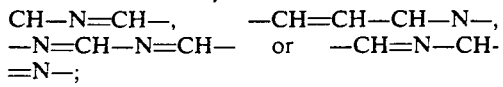

wherein one or two hydrogen atoms in said radicals $G^1$, $G^2$, $G^3$, $G^4$, $G^5$ or $G^6$ or in the benzene part of the radicals of formula (e-2), (e-3) or (e-9) may be replaced by $C_{1-6}$ alkyl, $C_{1-6}$ alkylthio, $C_{1-6}$ alkyloxy or halo where said hydrogen atom is bonded on a carbon atom, or by $C_{1-6}$ alkyl, $C_{1-6}$ alkyloxycarbonyl, $Ar^2$—$C_{1-6}$ alkyl, where said hydrogen is bonded on a nitrogen atom.

It is clear that $R^{11}$, $R^{12}$, $R^{17}$, $R^{18}$, $R^{19}$, $R^{20}$, $R^{21}$, $R^{22}$ or $R^{23}$ is absent where the radical of formula (e-1), respectively (e-4), (e-5), (e-6) or (e-7) is connected to $C_sH_{2s}$ on the atom bearing $R^{11}$, $R^{12}$, $R^{17}$, $R^{18}$, $R^{19}$, $R^{20}$, $R^{21}$, $R^{22}$ or $R^{23}$.

More particularly preferred compounds within the invention are those wherein L is a radical of formula (b-1).

Especially preferred compounds within the invention are those more particularly preferred compounds wherein Het is as described hereinabove for the particularly preferred compounds, wherein r is 0 and $L^1$ is hydrogen, hydroxy, $C_{1-6}$ alkyloxy, $C_{1-6}$ alkylthio, mercapto, Het, $Ar^1$, isocyanato, isothiocyanato or cyano.

More especially preferred compounds within the invention are those especially preferred compounds wherein $R^1$ is $C_{1-6}$ alkyl substituted with one $Ar^1$ radical.

It is evident that in the compounds of formula (I) wherein $L^1$ is Het, said Het may be unsaturated or partly or completely saturated.

The compounds of formula (I) wherein Het is a heterocycle which is substituted with a hydroxy, mercapto or amino radical may contain in their structure a keto-enol tautomeric system or a vinylog system thereof, and consequently these compounds may be present in their keto form as well as their enol form.

The compounds of formula (I) can generally be prepared by reacting a piperidine of formula (II) with a diamine of formula (III).

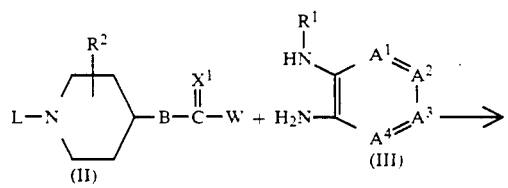

In some instances the reaction of (II) with (III) first yields an intermediate of formula

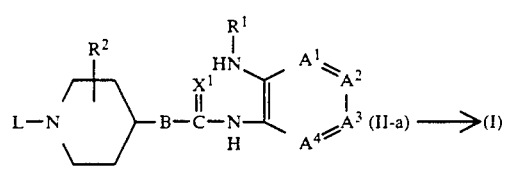

which may in situ or, if desired, after isolating and further purifying it, be cyclisized to the desired compounds of formula (I).

In (II) and (II-a) $X^1$ is O, S or NH.

W as used in the foregoing and following reaction schemes is an appropriate leaving group such as, for example, halo, e.g. chloro, bromo or iodo, a sulfonyloxy group, e.g. methylsulfonyloxy or 4-methylphenylsulfonyloxy, and where W is connected to a —C(=X)—, —C(=X$^1$)— or —C(=X$^2$)-radical it may also be $C_{1-6}$ alkyloxy, $C_{1-6}$ alkylthio, $Ar^2$—O—, or $Ar^2$—S—.

The piperidine of formula (II) may in situ be generated, for example, by converting a piperidine which is substituted in its 4-position with a —B—C(=X$^1$)—OH radical into a piperidine of formula (II) by reacting the former piperidine with thionyl chloride, phosphor trichloride, phosphoryl chloride, polyphosphoric acid, phosphoroxy chloride and the like.

The reaction of (II) with (III) may be conducted in a suitable solvent such as, for example, a hydrocarbon, e.g. benzene, hexane; an ether, e.g., 1,1'-oxybisethane, tetrahydrofuran; a ketone, e.g., 2-propanone, 2-butanone; an alcohol, e.g., methanol, ethanol, 2-propanol, 1-butanol; a halogenated hydrocarbon, e.g., trichloromethane, dichloromethane, an organic acid, e.g., acetic acid. propanoic acid; a polar aprotic solvent e.g., N,N-dimethylformamide, N,N-dimethylacetamide and the like; and mixtures of such solvents. Depending upon the solvent and nature of W it may be appropriate to add an appropriate base and/or a iodide salt, preferably an alkali metal iodide, to the reaction mixture. Elevated temperatures may enhance the reaction rate.

The compounds of formula (I) can also be prepared by reacting an intermediate of formula (V) with a piperidine of formula (IV) wherein $E^1$ and $E^2$ are selected so that during the reaction a radical —B— is formed.

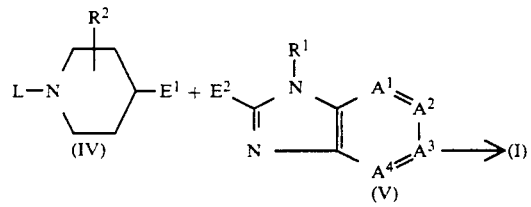

For example, the compounds of formula (I) can be prepared by reacting a piperidine of formula (IV) wherein $E^1$ is a radical of formula —B—M with an intermediate of formula (V) wherein $E^2$ is a radical of formula —W.

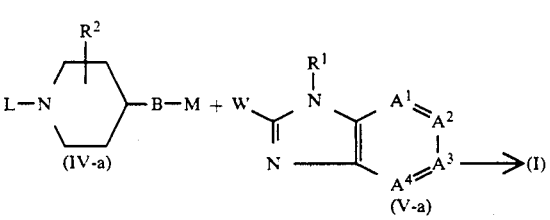

In (IV-a) M is, depending upon the nature of B, hydrogen or an appropriate alkalimetal or earth alkaline metal and in (V-a) W has the previously described meaning. Additionally, the compounds of formula (I) can also be prepared by reacting a piperidine of formula (IV) wherein $E^1$ is W with an intermediate of formula (V) wherein $E^2$ is a radical of formula —B—M, said W and M having the previously described meanings.

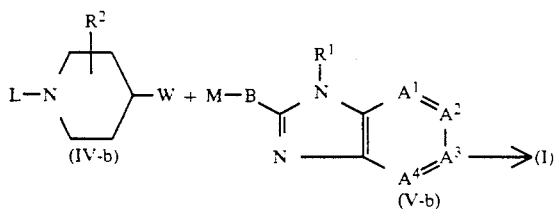

More particularly, the compounds of formula (I) wherein B is —CH₂— can also be prepared by reacting a piperidine of formula (IV) wherein $E^1$ represents a radical of formula —CH₂—W, (IV-c), with an intermediate of formula (V) wherein $E^2$ represents M, (V-c) or alternatively, by reacting a piperidine of formula IV, wherein $E^1$ is a radical of formula —M, (IV-d), with an intermediate of formula (V) wherein $E^2$ is a radical of formula —CH₂—W, (V-d).

Said cyclodesulfurization reaction may be carried out by the reaction of (VI-a) with an appropriate alkyl halide, preferably iodomethane in an appropriate reaction-inert organic solvent, e.g., a $C_{1-6}$ alkanol such as methanol, ethanol, 2-propanol and the like. Otherwise, the cyclodesulfurization reaction may be carried out by the reaction of (VI-a) with an appropriate metal oxide or salt in an appropriate solvent according to art-known procedures. For example. the compounds of formula (I) can easily be prepared by the reaction of (VI-a) with an

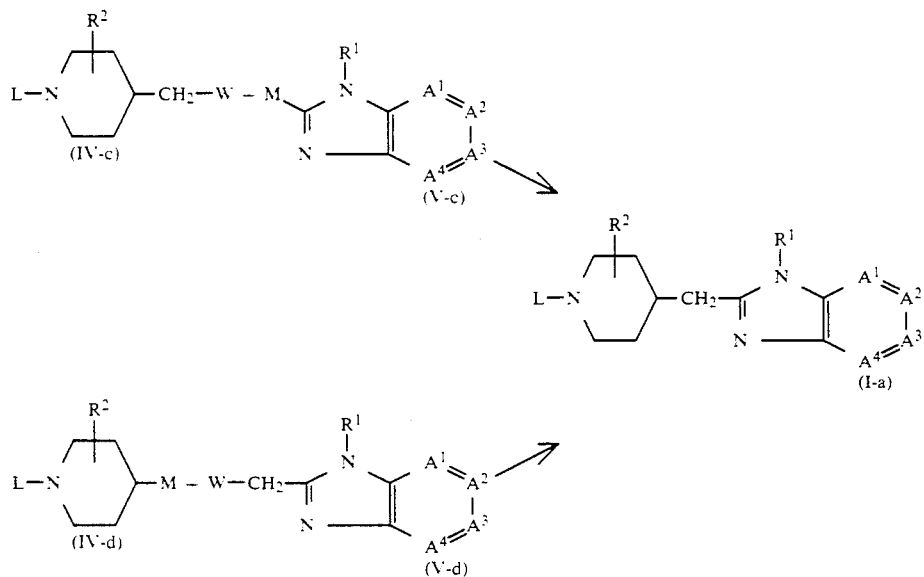

The reaction of (IV) with (V) may conveniently be conducted in an appropriate solvent such as for example, an aromatic hydrocarbon, e.g., benzene, methylbenzene; an ether, e.g. 1,4-dioxane, 1,1'-oxybisethane, tetrahydrofuran and the like; a halogenated hydrocarbon, e.g. trichloromethane and the like; N,N-dimethylformamide (DMF); N,N-dimethylacetamide (DMA); and where M is hydrogen, said solvent may also be a $C_{1-6}$ alkanol, e.g., methanol, ethanol, 1-butanol and the like; a ketone, e.g., 2-propanone, 4-methyl-2-pentanone and the like. In some circumstances, the addition of an appropriate base such as, for example, an alkali metal carbonate or hydrogen carbonate, sodium hydride or an organic base such as, for example, N,N-diethylethanamine or N-(1-methylethyl)-2-propanamine and/or the addition of a iodide salt, preferably an alkali metal iodide, may be appropriate. Somewhat elevated temperatures may enhance the rate of the reaction.

The compounds of formula (I), wherein B is NR, can also be prepared by a cyclodesulfurization reaction of an appropriate thiourea derivative of formula appropriate Hg(II) or Pb(II) oxide or salt, such as, for example HgO, HgCl₂, Hg(OAc)₂, PbO or Pb(OAc)₂. In certain instances it may be appropriate to supplement the reaction mixture with a small amount of sulfur. Even so methanediimines, especially N,N'-methanetetraylbis[cyclohexanamine] may be used as cyclodesulfurizing agents.

In some instances compounds of formula (I), wherein B is NR, may alternatively be prepared by cyclodesulfurizing a thiourea of formula (VI-b) and subsequently dehydrating the thus obtained oxazole[5,4-d]pyrimidine derivatives with a suitable dehydrating agent, e.g., phosphoryl chloride, phosphor trichloride, phosphor pentachloride, thionyl chloride and the like.

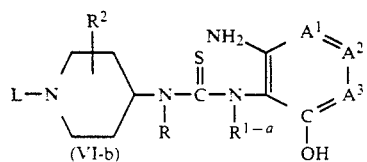

In (VI-b) $R^{1-a}$ has the same meaning as described hereinabove for $R^1$.

The compounds of formula (I) can also be converted into each other. A number of such reactions will be described hereinafter in more detail.

In order to simplify the structural representations of the compounds of formula (I) and of certain precursors and intermediates thereof the

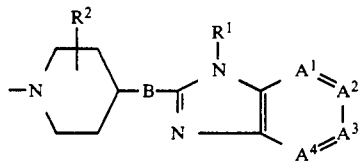

radical will hereafter be represented by the symbol D.

The compounds of formula (I) wherein L is $L^2$, said compounds being represented by the formula (I-b) can be prepared by alkylating an intermediate of formula (VII) with a compound of formula (I) wherein L is $Q^2$, said compound being represented by the formula (I-c).

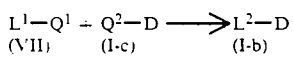

$L^2$ as defined hereinabove is a radical of formula (b-1) other than hydrogen, said radical being represented by the formula (b-1-a), or a radical of formula (b-2).

In (VII) and (I-c), $Q^1$ and $Q^2$ are selected so that a bivalent radical of formula (b-1-a) or (b-2) is formed during the alkylation reaction, said (b-1-a) and (b-2) having the previously described meaning.

For example, the compounds of formula (I-b) can be prepared by N-alkylating a piperidine of formula (I-c) wherein $Q^2$ is hydrogen, said piperidine being represented by the formula (I-c-1), with a reagent of formula (VII-a).

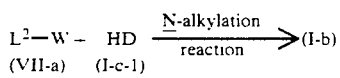

In some instances the alkylating reagent (VII-a) can also be a reactive cyclic reagent which may be formed by an intramolecular cyclisation reaction. The said cyclic form of (VII-a) may be formed in situ, or if desired, isolated and further purified before reacting it with (I-c-1).

Additionally, the compounds of formula (I-b), wherein $L^2$ is a radical of formula (b-1-a), wherein T is $T^2$, said $T^2$ being O, S, $NR^3$ or $-Z^1-C(=X)-Y-$, said $Z^1$ being O, S or $NR^5$, or a radical of formula (b-2) wherein $T^1$ is $T^3$, said $T^3$ being $-Z^1-C(=X)-$ or a direct bond, said compounds being represented by the formulae (I-b-1-a), respectively (I-b-1-b), can be prepared by alkylating a piperidine of formula (1-c-2) with a reagent of formula (VII-b).

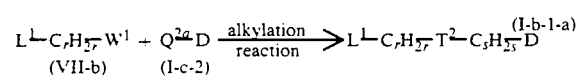

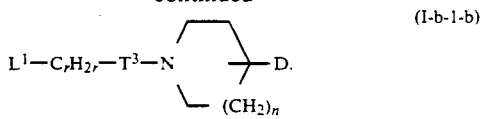

In (I-c-2) $Q^{2a}$ is a radical of formula $HT^2-C_sH_{2s}-$, respectively a radical of formula

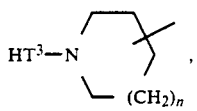

and $W^1$ has the previously defined meaning of W, and where r=0, and $L^1$ is Het or $Ar^1$, it may also be $C_{1-6}$ alkyloxy or $C_{1-6}$ alkylthio.

The compounds of formula (I-b), wherein $L^2$ is a radical of formula (b-1-a), wherein T is $T^4$, said $T^4$ being O, S, $NR^3$ or $-Z-C(=X)-Y^1-$, said $Y^1$ being O, S or $NR^3$, and said compounds being represented by the formula (I-b-2), may also be prepared by alkylating a piperidine of formula (I-c) wherein $Q^2$ is a radical of formula $-C_sH_{2s}-W$, said piperidine being represented by the formula (I-c-3), with a reagent of formula (VII) wherein $Q^1$ is a radical of formula $-C_rH_{2r}-T^4H$, said reagent being represented by the formula (VII-c).

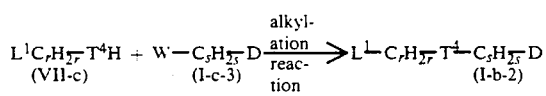

The alkylation reactions are conveniently conducted in an inert organic solvent such as, for example, an aromatic hydrocarbon, e.g., benzene, methylbenzene, dimethylbenzene, and the like; a $C_{1-6}$ alkanol, e.g., methanol, ethanol, 1-butanol and the like; a ketone, e.g., 2-propanone, 4-methyl-2-pentanone and the like; an ether, e.g., 1,4-dioxane, 1,1'-oxybisethane, tetrahydrofuran and the like; N,N-dimethylformamide (DMF); N,N-dimethylacetamide (DMA); dimethyl sulfoxide (DMSO); nitrobenzene; 1-methyl-2-pyrrolidinone; and the like. The addition of an appropriate base such as, for example, an alkali metal carbonate or hydrogen carbonate, sodium hydride or an organic base such as, for example, N,N-diethylethanamine or N-(1-methylethyl)-2-propanamine may be utilized to pick up the acid which is liberated during the course of the reaction. In some circumstances the addition of a iodide salt, preferably an alkali metal iodide, is appropriate. Somewhat elevated temperatures may enhance the rate of the reaction.

The compounds of formula (I-b) can also be prepared by the reductive N-alkylation reaction of (I-c-1) with an appropriate carbonyl-compound of formula $L^{2-a}=C=O$ (VIII), said $L^{2-a}=C=O$ being a compound of formula $L^2-H$ wherein a $-CH_2-$ radical is oxidated to a carbonyl radical.

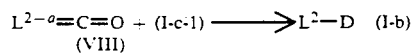

The compounds of formula (I-b), wherein $L^2$ is a radical of formula $L^1-C_rH_{2r}-NR^3-C_sH_{2s}-$, said compounds being represented by the formula (I-b-3)

may alternatively be prepared by the reductive N-alkylation reaction of a compound of formula (I), wherein L is a radical of formula $HN(R^3)-C_sH_{2s}-$, (I-d), with an appropriate carbonyl-compound of formula $L^1-(C_rH_{2r-1})=O$, (IX), said $L^1-(C_rH_{2r-1})=O$ being a compound of formula $L^1-C_rH_{2r}-H$ wherein a $-CH_2-$ radical is oxidated to a carbonyl radical. The compounds of formula (I-b-3) can also be prepared by the reductive N-alkylation of an amine of formula (X), with a compound of formula (I) wherein L is a radical of formula $O=(C_sH_{2s-1})-$, said compound being represented by the formula (I-e), and said $O=(C_sH_{2s-1})-$ being a radical of formula $H-C_sH_{2s}-$ wherein a $-CH_2-$ radical is oxidated to a carbonyl radical.

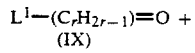

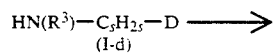

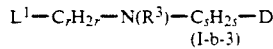

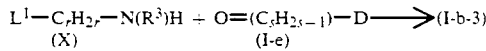

Said reductive N-alkylation reaction may conveniently be carried out by catalytically hydrogenating a mixture of the reactants in a suitable reaction-inert organic solvent according to art-known catalytic hydrogenating procedures. The reaction mixture may be stirred and/or heated in order to enhance the reaction rate. Suitable solvents are, for example, water; $C_{1-6}$ alkanols, e.g. methanol, ethanol, 2-propanol and the like; cyclic ethers, e.g. 1,4-dioxane and the like; halogenated hydrocarbons, e.g. trichloromethane and the like; N,N-dimethylformamide; dimethyl sulfoxide and the like; or a mixture of 2 or more of such solvents. The term "art-known catalytic hydrogenating procedures" means that the reaction is carried out under hydrogen atmosphere and in the presence of an appropriate catalyst such as, for example, palladium-on-charcoal, platinum-on-charcoal and the like. In order to prevent the undesired further hydrogenation of certain functional groups in the reactants and the reaction products it may be advantageous to add an appropriate catalyst-poison to the reaction mixture, e.g., thiophene and the like.

The compounds of formula (I-b), wherein L is a radical of formula (b-1-a) wherein T is $Z^1-C(=X^2)-NH-$, $Z^1$ being as previously described, $X^2$ being O or S, and said compounds being represented by the formula (I-b-4), can generally be prepared by reacting an isocyanate or isothiocyanate of formula (I-f) with a reagent of formula (XI):

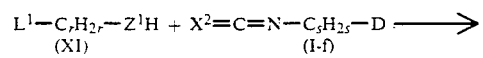

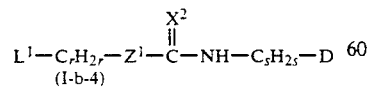

The compounds of formula (I-b), wherein $L^2$ is a radical of formula (b-1-a), wherein T is $-NH-C(=X^2)-Y^1-$, $Y^1$ being as previously described, and the compounds of formula (I-b), wherein $L^2$ is a radical of formula (b-1-a), wherein T is $-NH-C(=X^2)-$ and s is 0, and the compounds of formula (I-b), wherein $L^2$ is a radical of formula (b-2), wherein $T^1$ is $-NH-C(=X^2)-$, said compounds being represented by the formula (I-b-5-a), respectively (I-b-5-b) and (I-b-5-c), can be prepared by reacting an isocyanate or isothiocyanate of formula (XII) with a piperidine of formula (I-c-4), respectively (I-c-1) and (I-c-5).

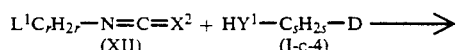

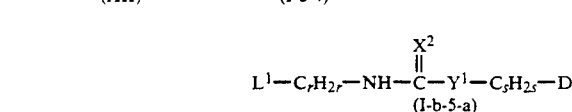

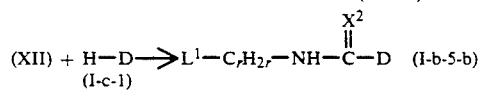

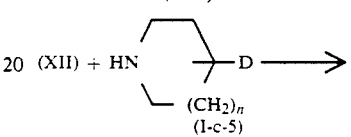

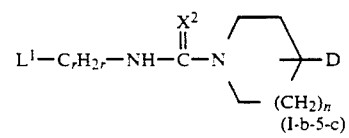

The reaction of (XI) with (I-f) and of (XII) with (I-c-4), respectively (I-c-1) and (I-c-5) may be conducted in a suitable reaction-inert solvent such as, for example, a hydrocarbon, e.g., benzene, a ketone, e.g., acetone, a halogenated hydrocarbon, e.g., dichloromethane, trichloromethane, an ether, e.g., 1,1'-oxybisethane, tetrahydrofuran and the like. Elevated temperatures may be suitable to enhance the rate of the reaction.

The compounds of formula (I-b), wherein $L^2$ is a radical of formula (b-1-a), wherein T is $-C(=X^2)-Y^1-$, and the compounds of formula (I-b), wherein L is a radical of formula (b-1-a), wherein s is 0 and T is a radical of formula $-C(=X^2)-$, and the compounds of formula (I-b) wherein $L^2$ is a radical of formula (b-2), wherein $T^1$ is $-C(=X^2)-$, said compounds being represented by the formula (I-b-6-a), respectively (I-b-6-b) and (I-b-6-c), may be prepared by reacting a piperidine of formula (I-c-4), respectively (I-c-1) and (I-c-5) with a reagent of formula (XIII).

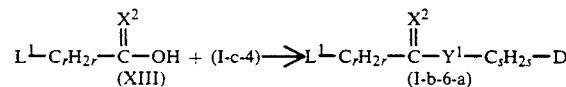

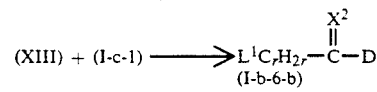

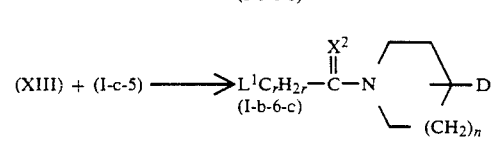

The reaction of (XIII) with (I-c-4), respectively (I-c-1) and (1-c-5) may generally be conducted following art-known esterification- or amidation reaction-procedures. For example, the carboxylic acid may be converted into a reactive derivative, e.g., an anhydride or a carboxylic acid halide, which subsequently, is reacted with (I-c-4), (I-c-1) or (I-c-5); or by reacting (XIII) and (I-c-4), respectively (I-c-1) and (I-c-5) with a suitable reagent capable of forming amides or esters, e.g., dicyclohexylcarbodiimide, 2-chloro-1-methylpyridinium iodide and the like. Said reactions are most conveniently conducted in a suitable solvent such as, for example, an ether, e.g. tetrahydrofuran, a halogenated hydrocarbon, e.g. dichloromethane, trichloromethane or a polar aprotic solvent, e.g. N,N-dimethylformamide. The addition of a base, e.g. N,N-diethylethanamine may be appropriate.

The compounds of formula (I-b), wherein $L^2$ is a radical of formula (b-1-a) wherein T is $-Z^1-C(=X)-Y^1-$, and the compounds of formula (I-b), wherein $L^2$ is a radical of formula (b-1-a) wherein s is 0 and T is $-Z^1-(C=X)-$, and the compounds of formula (I-b), wherein $L^2$ is a radical of formula (b-2) wherein $T^1$ is $-Z^1-C(=X)-$, said compounds being represented by the formula (I-b-7-a), respectively (I-b-7-b) and (I-b-7-c), can also be prepared by reacting (XI) with (I-c-4), respectively (I-c-1) and (I-c-5) in the presence of an appropriate $>C=X$ generating agent.

(XI) + (I-c-4) +

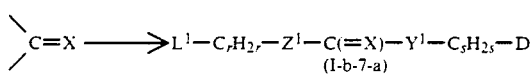
(I-b-7-a)

generating agent (XI) + (I-c-1) +

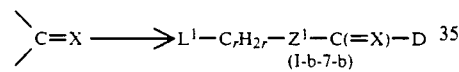
(I-b-7-b)

generating agent (XI) + (I-c-5) +

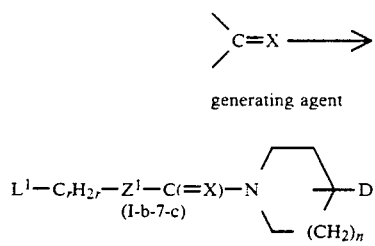
(I-b-7-c)

An appropriate $>C=X$ generating agent is, for example, 1,1'-thiocarbonylbis[1H-imidazole], 1,1'-carbonylbis[1H-imidazole], carbonic dichloride, carbonothioic dichloride, urea, thiourea, trichloroacetyl chloride, and the like. The reaction of (XI) with (I-c-4), (I-c-1) or (I-c-5) is conveniently conducted in a suitable solvent, such as, for example, a hydrocarbon, e.g., benzene, methylbenzene; an ether, e.g., 1,1'-oxybisethane, tetrahydrofuran; a halogenated hydrocarbon, e.g., dichloromethane, trichloromethane and the like. The addition of a base such as, for example, an alkali metal carbonate or hydrogen carbonate or an organic base, e.g., N,N-diethylethanamine and the like, may be appropriate.

The compounds of formula (I-b) wherein $L^2$ is a radical of formula (b-1), wherein s is an integer of from 2 to 6 inclusive, said compounds being represented by the formula (I-g) can be prepared by reacting an appropriate alkene of formula (XIV) with a piperidine of formula (I-c-1).

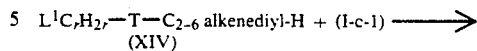

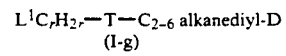
(I-g)

The compounds of formula (I-b) wherein $L^2$ is a radical of formula $L^1-C_rH_{2r}-T-C_{s'-2}H_{2s'-4}-CH(Y^1H)-CH_2-$, wherein s' is an integer of from 2 to 6 inclusive, said compounds being represented by the formula (I-h) may also be prepared by reacting a reagent of formula (XV) with a piperidine of formula (I-c-1).

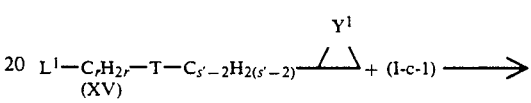

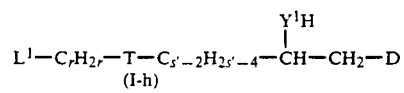
(I-h)

The reactions of (XIV) with (I-c-1), and (XV) with (I-c-1) may be conducted by stirring and, if desired, heating the reactants together. The said reactions may be conducted in a suitable solvent such as, for example, an alkanone, e.g. 2-propanone, 4-methyl-2-propanone, an ether, e.g. tetrahydrofuran, 1,1'-oxybisethane, an alcohol, e.g. methanol, ethanol, 1-butanol, N,N-dimethylformamide, N,N-dimethylacetamide and the like.

It is evident that the radical "$-C_{2-6}$ alkenyl—", the corresponding "$-C_{2-6}$ alkanediyl-" radical and the radical $C_{2s'-2}H_{2s'-4}$ may bear the previously described substitutions of the radical $-C_sH_{2s}-$.

The compounds of formula (I) wherein $L^1$ is Het, said compounds being represented by the formula (I-i), may also be prepared following procedures for preparing ring systems which are known in the art or analogous procedures thereof. A number of such cyclization procedures will be described hereinafter.

The bivalent radical K used in the description of these cyclization reactions has the following meaning:

 (d-1)

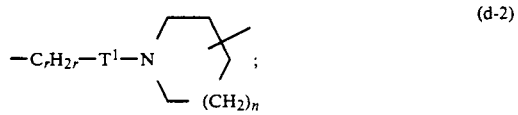 (d-2)

and the radicals (e-1-a), (e-2), (e-3), (e-5-a), (e-6), (e-7) and (e-8) also used in the description of these cyclization reactions have the following meaning:

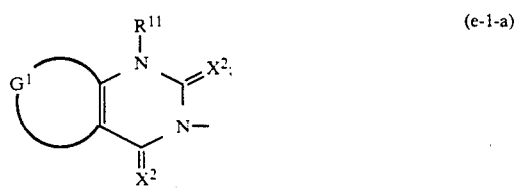 (e-1-a)

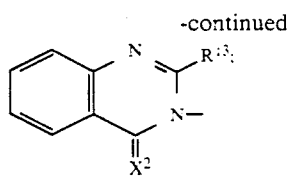 (e-2)

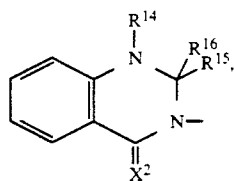 (e-3)

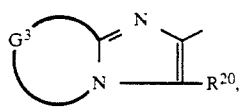 (e-5-a)

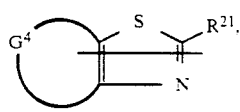 (e-6)

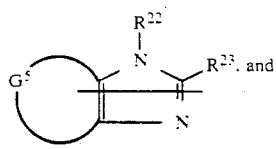 (e-7)

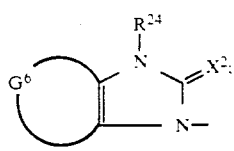 (e-8)

wherein $X^2$, $R^{11}$, $R^{13}$, $R^{14}$, $R^{15}$, $R^{16}$, $R^{20}$, $R^{21}$, $R^{22}$, $R^{23}$, $R^{24}$, $G^1$, $G^3$, $G^4$, $G^5$ and $G^6$ have the same meaning as defined hereinabove for the particularly preferred compounds.

For example, the compounds of formula (I-i) wherein Het is an optionally substituted imidazolyl radical, said compounds being represented by the formula (I-i-1), can be prepared by the cyclization reaction of an appropriate N-(2,2-diC$_{1-6}$alkyloxyethyl)imidamide derivative of formula (XVI).

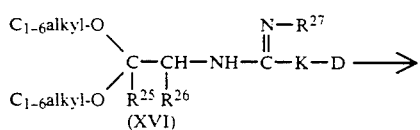

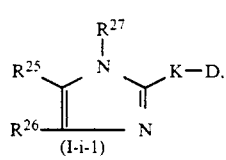

wherein $R^{25}$, $R^{26}$ and $R^{27}$ are each independently optional substituents of the imidazole ring.

Said cyclization reaction may conveniently be conducted in a suitable solvent in the presence of an appropriate acid such as, for example, hydrochloric, hydrobromic and the like acids. Elevated temperatures may enhance the rate of the reaction.

The compounds of formula (1-i) wherein Het is an optionally substituted thiazolyl radical, being optionally condensed with a five- or six-membered hetero- or carbocyclic ring, may be prepared by a number of cyclization reactions, yielding, depending upon the case, compounds which may be represented by the formula (I-i-2) or (I-i-3).

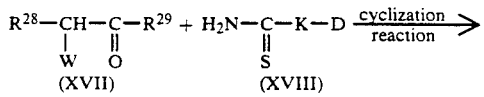

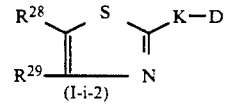

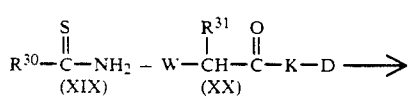

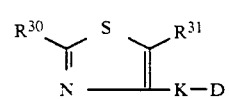

$R^{28}$, $R^{29}$, $R^{30}$ and $R^{31}$ are each independently optional substituents of the said thiazolyl ring, or, where in the compounds of formula (I-i-2) said thiazolyl ring is condensed with a five- or six-membered hetero- or carbocyclic ring, $R^{28}$ and $R^{29}$ taken together may form a bivalent radical of formula $G^4$.

Further, where Het is a radical of formula (e-1-a), said Het may be formed by condensing an intermediate (XXI) with a $>C=X^2$ generating agent, e.g. urea, thiourea, 1,1'-carbonylbis[1H-imidazole], C$_{1-6}$ alkyl carbonohalidate, phosgene, thiophosgene, trichloromethyl carbonohalidate and the like.

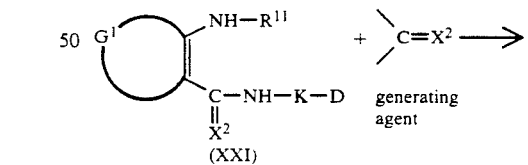

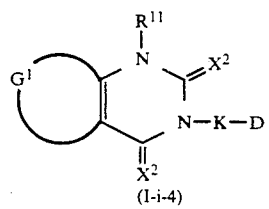

The compounds of formula (I-i-4) wherein $R^{11}$ is hydrogen may additionally be prepared by cyclizing an intermediate of formula

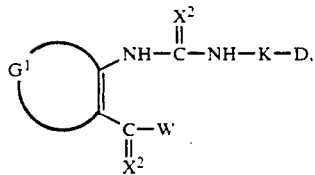

which may in situ be generated by reacting a reagent (XXIII) with an amine (XXIV).

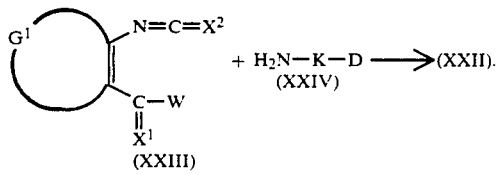

The reaction of (XXI) with the >C=$X^2$ generating agent and the cyclization of (XXII) may conveniently be conducted in a suitable solvent such as, for example, an ether, e.g. 1,1-oxybisethane, tetrahydrofuran, an halogenated hydrocarbon, e.g. dichloromethane, trichloromethane, a hydrocarbon, e.g. benzene, methylbenzene, an alcohol, e.g. methanol, ethanol, a ketone, e.g. 2-propanone, 4-methyl-2-pentanone, N,N-dimethylformamide, N,N-dimethylacetamide, or mixtures of such solvents, optionally in the presence of an appropriate base such as, for example, N,N-diethylethanamine, an alkali or earth alkaline metal carbonate or hydrogen carbonate. In order to enhance the reaction rate, it may be suitable to heat the reaction mixture.

Further, where Het is a radical of formula (e-2), said Het may be generated by cyclizing an intermediate (XXV) with an acid (XXVI) or a suitable functional derivative thereof, thus preparing a compound of formula (I-i-5). Alternatively an intermediate (XXVII) may be condensed with an aromatic amino acid or -thioacid of formula (XXVIII), preparing also a compound (I-i-5).

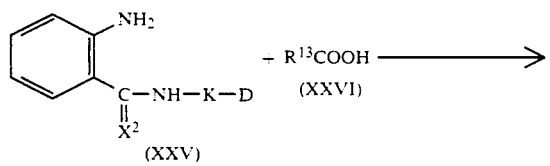

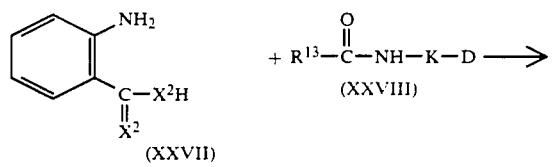

The reaction of (XXV) with (XXVI) and of (XXVII) with (XXVIII) may be conducted in a suitable reaction-inert solvent, such as, for example, a hydrocarbon, e.g. benzene, methylbenzene, an alcohol, water. In some instances it may be appropriate to use higher temperatures in order to reduce the reaction time.

Where Het is a radical of formula (e-3), wherein $R^{16}$ is hydrogen and $R^{15}$ is a radical of formula $R^{15-a}$—$CH_2$—, said Het may be formed by reacting a compound (XXIX) with an appropriate acetylene derivative (XXX), thus preparing a compound of formula (I-i-6).

Additionally, where Het is a radical of formula (e-3), said Het may be formed by reacting (XXIX) with a ketone of formula (XXXI), thus preparing a compound of formula (I-i-7).

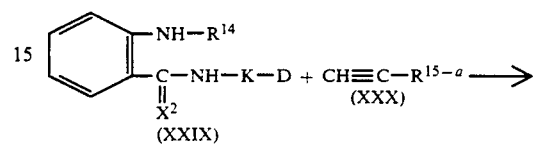

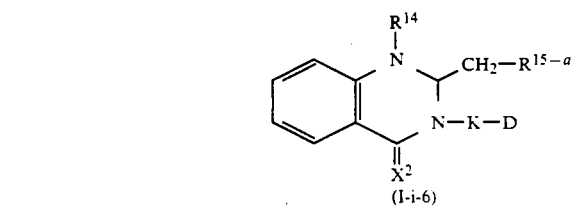

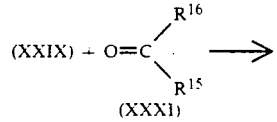

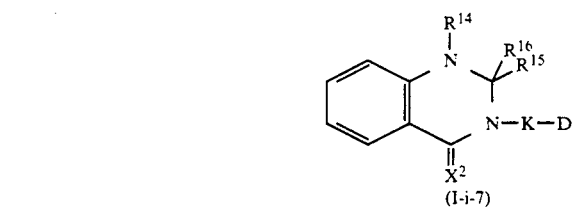

The reaction of (XXIX) with (XXX) may be conducted in a suitable solvent such as, for example, an alcohol, e.g. methanol, ethanol, while the reaction of (XXIX) with (XXXI) may be conducted in a suitable solvent preferably in the presence of an organic acid such as, for example, ethanedioic acid and the like. Elevated temperatures may also be appropriate to shorten the reaction time.

Additionally, where Het is a radical (e-5-a), said Het may be created by condensing a reagent (XXXII) with an intermediate (XXXIII), thus giving a compound (1-i-8).

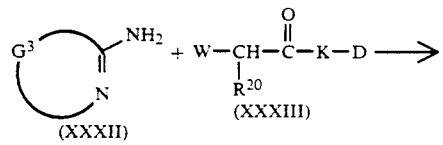

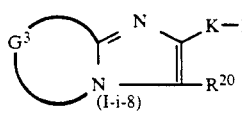

Where Het is a radical (e-6) being connected to K by the $G^4$ containing ring and bearing a 2-mercaptosubstituent, said Het may be formed during the cyclization of an intermediate (XXXII) with $CS_2$, thus preparing a compound (I-i-9).

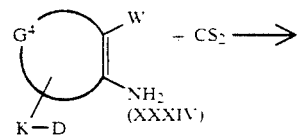

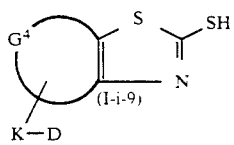

Where Het is a radical of formula (e-7) being connected to K either by the $G^5$ containing ring or by the imidazole ring, said Het is formed during the condensation reaction of a reagent (XXXV) with an intermediate (XXXVI) respectively by the cyclodesulfurization reaction of an intermediate (XXXVII), thus preparing a compound (I-i-10) respectively (I-i-11).

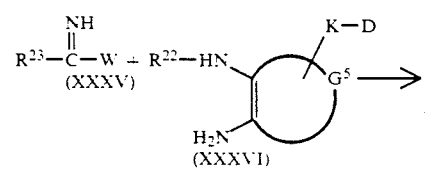

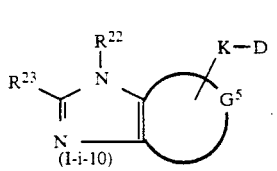

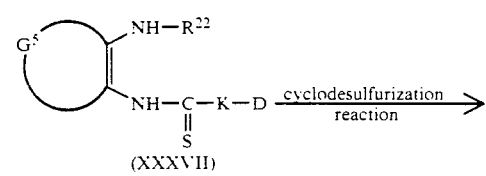

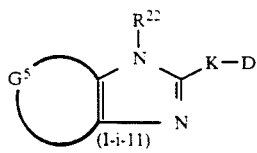

The reactions of (XXXII) with (XXXIII), of (XXXIV) with $CS_2$ and (XXXV) with (XXXVI) may conveniently conducted in a suitable reaction-inert solvent, such as for example one of the solvents given hereinabove for the preparation of (I-i-4) optionally in the presence of an appropriate base, e.g. one of the bases also described for the preparation of (I-i-4); higher temperatures may be used to enhance the reaction rate.

The cyclodesulfurization of (XXXVII) may be carried out by the reaction of (XXXVII) with an appropriate alkyl halide, preferably iodomethane in an appropriate reaction-inert organic solvent, e.g., a $C_{1-6}$ alkanol such as methanol, ethanol, 2-propanol and the like. Otherwise, the cyclodesulfurization reaction may be carried out by the reaction of (XXXVII) with an appropriate metal oxide or salt in an appropriate solvent according to art-known procedures. For example, the compounds of formula (I) can easily be prepared by the reaction of (XXXVII) with an appropriate Hg(II) or Pb(II) oxide or salt, such as, for example HgO, $HgCl_2$, $Hg(OAc)_2$, PbO or $Pb(OAc)_2$. In certain instances it may be appropriate to supplement the reaction mixture with a small amount of sulfur. Even so methanediimines, especially N,N'-methanetetraylbis[cyclohexanamine] may be used as cyclode-sulfurizing agents.

Where Het is a radical (e-8), said Het may be formed during the condensation of an intermediate (XXXVIII) with a $>C=X^2$ generating agent, following the same procedures as previously described for the preparation of (I-i-4) starting from (XXXIII).

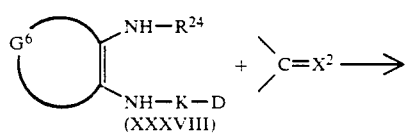

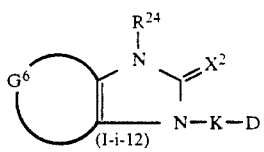

The compounds of formula (I) can also be converted into each other following art-known procedures of functional grouptransformation. Some examples will be cited hereinafter.

The compounds of formula (I), wherein —B— is —S— may be converted into the corresponding compounds of formula (I), wherein —B— is —SO— or —$SO_2$— by an appropriate oxidation reaction, e.g. by reacting the former compounds with a suitable oxidating agent such as, for example, potassium periodate, a peroxide, e.g. 3-chlorobenzenecarboperoxoic acid, hydrogen peroxide, and the like, in a suitable solvent such as, for example, an ether, e.g. tetrahydrofuran, 1,1'-oxybisethane, a hydrocarbon, e.g. benzene, a halogenated hydrocarbon, e.g. dichloromethane, trichloromethane and the like. In the instance where a sulfinyl is desired, said oxidation reaction is preferably conducted at lower temperatures with approximately one equivalent of the oxidating agent, while where a sulfonyl is desired, said oxidation reaction may be conducted at room or elevated temperature with an excess of oxidating agent.

The compounds of formula (I) having a nitro substituent can be converted into the corresponding amines by stirring and, if desired, heating the starting nitro-compounds in a hydrogen-containing medium in the presence of a suitable amount of an appropriate catalyst such as, for example, platinum-on-charcoal, palladium-on-charcoal, Raney-nickel and the like catalysts. Suitable solvents are, for example, alcohols, e.g., methanol, ethanol and the like.

In an analogous procedure, the compounds of formula (I) having a cyano substituent, can be converted into the corresponding aminomethyl containing compounds.

The compounds of formula (I) having an hydroxy substituent may be converted into the corresponding halo compounds following art-known halogenating procedures, e.g., by reacting the former compounds with a suitable halogenating agent. e.g. thionyl chloride, phosphoryl chloride, phosphor trichloride, phosphor pentachloride, thionyl bromide, phosphor tribromide and the like.

The compounds of formula (I) containing an ester group may be converted into the corresponding carboxylic acids following art-known saponification procedures. e.g. by treating the said compounds with an aqueous alkaline solution or with an aqueous acidic solution.

The compounds of formula (I) containing a Het substituted with a thioxo group can be converted into the corresponding oxo compounds following art-known procedures, for example, by treating the said thioxo containing compounds with a peroxide, e.g. hydrogen peroxide in a suitable alkaline medium. e.g. an aqueous alkali metal hydroxide solution which may be mixed with an organic solvent such as, for example, methanol, ethanol and the like.

The compounds of formula (I) containing an unsaturated Het can be converted into the corresponding saturated form following art-known reducing procedures, e.g. by treating the said compounds with hydrogen in the Presence of a suitable catalyst such as, for example, platinum-on-charcoal. Palladium-on-charcoal an the like catalysts.

Halo atoms substituted on aryl groups may be replaced by hydrogen following art-known hydrogenolysis procedures, i.e. by stirring and, if desired, heating the starting compounds in a suitable solvent under hydrogen atmosphere in the presence of an appropriate catalyst. e.g. palladium-on-charcoal and the like catalysts. Said halo atoms may also be replaced by a $C_{1-6}$ alkyloxy or a $C_{1-6}$ alkylthio substituent by reacting the starting halo-compound with an appropriate alcohol or thioalcohol or, preferably, an alkali- or earth alkaline metal salt or an appropriate alcohol or thioalcohol in a suitable solvent. Said halo atoms may also be replaced by a hydroxy substituent by treating the starting compounds with an aqueous acidic solution, e.g. an aqueous hydrochloric or hydrobromic solution.

$C_{1-6}$ alkyloxy and $C_{1-6}$ alkylthio radicals substituted on aryl may be converted into the corresponding hydroxy or thiol radicals by treating them with an aqueous acidic solution. e.g. an aqueous hydrochloric or hydrobromic solution.

The compounds of formula (I) containing an imino group, e.g. where $NR^1$, $NR^3$, $NR^4$ or $NR^5$ is NH, or an amino group, e.g. where $AR^1$, $AR^2$ or Het is substituted with an amino group, the hydrogen atom in said imino or amino may be replaced by a suitable substituent following art-known procedures such as, for example, N-alkylation, reductive N-alkylation, acylation and the like methods. A number of such procedures will be described hereinafter in more detail. For example, $C_{1-6}$ alkyl groups or substituted $C_{1-6}$ alkyl groups may be introduced by reacting the starting compounds with an appropriate N-alkylating agent following the procedures described hereinabove for the N-alkylation reactions of (VII) with (I-c), or by reacting the starting compounds with an appropriate carbonyl-compound following the reductive N-alkylation procedures described hereinabove for the reductive N-alkylations of (I-c-1) with (VIII), (I-d) with (IX) and (I-e) with (X).

$C_{1-6}$ alkylcarbonyl, $Ar^2$-carbonyl and the like groups may be introduced by reacting the starting amine with an appropriate carboxylic acid or a derivative thereof such as, for example, an acid halide, acid anhydride and the like.

$C_{1-6}$ alkyloxycarbonyl and $Ar^2$-oxycarbonyl groups can be introduced by reacting the starting amine compound with an appropriate carbonohalidate, e.g. ethyl carbonohalidate, phenylmethyl carbonohalidate and the like.

$Ar^2$—NH—CO, $Ar^2$—NH—CS, ($C_{1-6}$ alkylamino)—CO— ($C_{1-6}$ alkylamino)—CS—, and the like groups can conveniently introduced by reacting the starting amine compound with an appropriate isocyanate or isothiocyanate following the procedures described hereinabove for the Preparation of (I-b-4), (I-b-5-a), (I-b-5-b) and (I-b-5-c).

The compounds of formula (I) containing a substituted nitrogen atom may be converted into the corresponding compounds of formula (I) wherein said nitrogen bears a hydrogen atom following art-known methods for preparing N-H groups such as, for example:

1. where said nitrogen is substituted with an $Ar^2$-$CH_2$ group, by treating the starting compounds with hydrogen in the presence of a suitable catalyst, e.g. palladium-on-charcoal, platinum-on-charcoal, in an appropriate solvent;

2. or, where said nitrogen is substituted with a sulfonyl group, e.g. $C_{1-6}$ alkylsulfonyl and $Ar^2$-sulfonyl, by treating the starting compounds with an aqueous acidic solution preferably in the presence of a catalyst such as, for example, phenol, methoxybenzene and the like;

3. or, where said nitrogen atoms are substituted with an $Ar^2$-carbonyl group by treating the starting compounds with an aqueous basic solution. e.g. an alkali metal hydroxide solution;

4. where said nitrogen is substituted with $C_{1-6}$ alkyloxy carbonyl or $Ar^2$-oxycarbonyl, by treating the starting compounds with an aqueous acidic or aqueous basic solution optionally in admixture with an organic solvent or where said nitrogen atom is substituted with $Ar^2$-oxycarbonyl, by catalytically hydrogenating the starting materials in a suitable solvent.

The compounds of formula (I) containing a nitro9en atom substituted with $Ar^2$—$CH_2$— may be converted into the corresponding compounds where said nitro9en is substituted with $C_{1-6}$ alkyloxycarbonyl, for example by treating the former compounds with a $C_{1-6}$ alkyl carbonohalidate in the presence of a suitable solvent and, if desired, in the presence of an appropriate base.

The compounds of formula (I) containing a mercapto group may be converted into the corresponding isothiocyanato containing compounds by treating the starting amino compounds with $CS_2$ in the presence of N,N'-methanetetraylbis[cyclohexanamine].

The compounds of formula (I) containing a —CH$_2$—C(=O)— fragment can be converted into the corresponding compounds of formula (I) containing a —CH(halo)—C(=O)— fragment following art-known halogenating procedures, e.g. by treating the starting compound with a halogen.

In all of the foregoing and in the following preparations, the reaction products may be isolated from the reaction mixture and, if necessary, further purified according to methodologies generally known in the art.

The compounds of formula (I) have basic properties and, consequently, they may be converted to their therapeutically active non-toxic acid addition salt forms by treatment with appropriate acids, such as, for example, inorganic acids, such as hydrohalic acid. e.g. hydrochloric, hydrobromic and the like, and sulfuric acid, nitric acid, phosphoric acid and the like; or organic acids, such as. for example. acetic, propanoic, hydroxyacetic, 2-hydroxypropanoic, 2-oxopropanoic, ethanedioic, propanedioic, butanedioic, (Z)-2-butenedioic, (E)-2-butenedioic. 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely the salt form can be converted by treatment with alkali into the free base form.

Some intermediates and starting materials in the foregoing preparations are known compounds which may be prepared according to art-known methodologies of preparing said or similar compounds and others are new. A number of such preparation methods will be described hereinafter in more detail.

The intermediates of formula (II), wherein B is $CH_2.X^1$ is NH and W is $C_{1-6}$ alkyloxy, said intermediates being represented by the formula (II-c), can be prepared by reacting a (cyanomethyl)piperidine of formula (XXXIX) with an alcohol. e.g. methanol, ethanol and the like, in the presence of an acid, e.g. hydrochloric acid.

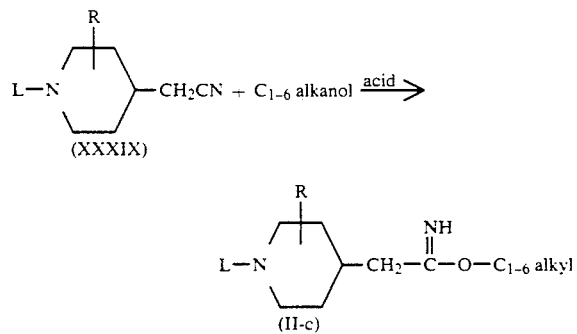

The intermediates of formula (IV) may be prepared by a reduction reaction of an appropriate 4-piperidinone, and, if desired, followed by an appropriate art-known groupstransformation procedure. e.g. where a compound of formula (V-b) is desired, by reacting the thus obtained alcohol with thionyl chloride, methylsulfonyl chloride and the like in order to obtain an appropriate leaving group.

The intermediates of formula (VI-a) can be prepared by the procedures described in, for example, European patent Publication Nos. 0,099,139; 0,145,037 and 0,144,101.

The intermediates of formula (VII) can conveniently be prepared following art-known procedures as described in, for example, U.S. Pat. No. 4,335,127, U.S. Pat. No. 4,342,870 and European Patent publication Number 0,070,053.

From formula (I) it is evident that the compounds of this invention may have several asymmetric carbon atoms in their structure. Each of these chiral centers may be present in a R- and a S-configuration, this R- and S-notation being in correspondence with the rules described by R. S. Cahn, C. Ingold and V. Prelog in Angew. Chem., Int. Ed. Engl., 5,385,511 (1966).

Pure stereochemically isomeric forms of the compounds of formula (I) may be obtained by the application of art-known procedures. Diastereoisomers may be separated by physical separation methods such as selective crystallization and chromatographic techniques, e.g., counter current distribution, and enantiomers may be separated from each other by the selective crystallization of their diastereomeric salts with optically active acids.

Pure stereochemically isomeric forms may also be derived from the corresponding pure stereochemically isomeric forms of the appropriate starting materials, provided that the reaction occurs stereospecifically.

It is evident that the cis and trans diastereomeric racemates may be further resolved into their optical isomers, cis(+), cis(−), trans(+) and trans(−) by the application of methodologies known to those skilled in the art.

Stereochemically isomeric forms of the compounds of formula (I) are naturally intended to be embraced within the scope of the invention.

The compounds of the present invention possess useful pharmacological properties and are active as antihistamines and as serotonin-antagonists. This is clearly demonstrated by the results of the "Protection of rats from compound 48/80-induced lethality" test.

In view of their antihistaminic properties, the compounds of formula (I) and their acid-addition salts are very useful in the treatment of allergic diseases such as, for example, allergic rhinitis, allergic conjunctivities, chronic urticaria, allergic astma and the like.

In view of their useful pharmacological properties the subject compounds may be formulated into various Pharmaceutical forms for administration purposes. To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably. for administration orally, rectally, percutaneously, or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars. kaolin, lubricants, binders, disintegrating agents and the like in the case of powders, pills, capsules and tablets, because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wettable agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways. e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

The present invention is also related with a method of treating allergic diseases in warm-blooded animals suffering from said allergic diseases by administering an effective anti-allergic amount of a compound of formula (I) or a pharmaceutically acceptable acid addition salt thereof.

Those of skill in treating allergic diseases in warm-blooded animals could easily determine the effective amount from the test results presented hereinafter. In general it is contemplated that an effective amount would be from 0.1 mg to 100 mg, more preferably from 1 to 50 mg.

The following examples are intented to illustrate and not to limit the scope of the present invention in all its aspects. Unless otherwise stated all parts therein are by weight.

EXPERIMENTAL PART

A. Preparation of Intermediates

Example 1

A mixture of 3.7 parts of 2-pyridinemethanamine, 4.1 parts of 4,6-dichloropyrimidin-5-amine, 3.03 parts of N,N-diethylethanamine and 150 parts of water was stirred for 8 hours at room temperature. After cooling, the whole was stirred overnight. The product was filtered off, washed with water and dried overnight in vacuo at 80° C., yielding 5.35 parts (90.8%) of 6-chloro-$N^4$-(2-pyridinylmethyl)-4,5-pyrimidinediamine; mp. 140.3° C. (interm. 1).

In a similar manner there were also prepared:

6-chloro-$N^4$-[(4-(4-fluorophenyl)methyl]-4,5-pyrimidinediamine: mp. 244.4° C. (interm. 2);
6-chloro-$N^4$-(2-furanylmethyl)-4,5-pyrimidinediamine mp. 138.7° C. (interm. 3);
6-chloro-$N^4$-(2-thienylmethyl)-4,5-pyrimidinediamine; mp. 165.5° C. (interm. 4);
6-chloro-$N^4$-[(5-methyl-2-furanyl)methyl]-4,5-pyrimidinediamine (interm. 5);
6-chloro-$N^4$-(2-pyrazinylmethyl)-4,5-pyrimidinediamine (interm. 6);
6-chloro-$N^4$-(4-thiazolylmethyl)-4,5-pyrimidinediamine; mp. 145.5° C. (interm. 7);
6-chloro-$N^4$-[(4-methoxyphenyl)methyl]-4,5-pyrimidinediamine; mp. 183.5° C. (interm. 8); and
$N^4$-[(4-fluorophenyl)methyl]-6-methyl-4,5-pyrimidinediamine: (interm. 9).

In a similar manner there is also prepared: 6-chloro-$N^4$-[(2,4-dimethylphenyl)methyl]-4,5-pyrimidinediamine; (interm. 10).

Example 2

To a stirred mixture of 20.2 parts of 4,5-pyrimidinediamine, 40 parts of pyridine and 144 parts of N,N-dimethylformamide was added dropwise a solution of 24.2 parts of 4-fluorobenzoyl chloride in 36 parts of N,N-dimethylformamide at 10° C. Upon completion, stirring was continued for 30 minutes at room temperature. 600 Parts of water were added. The product was filtered off and dried, yielding 30 parts (70%) of N-(4-amino-5-pyrimidinyl)-4-fluorobenzamide (interm. 11).

To a stirred mixture of 30 parts of N-(4-amino-5-pyrimidinyl)-4-fluorobenzamide and 360 parts of tetrahydrofuran were added portionwise 9.86 parts of lithium tetrahydroaluminate under nitrogen atmosphere. The mixture was stirred for 6 hours. Another portion of 10 parts of lithium tetrahydroaluminate was added portionwise and stirring was continued for 2 hours at room temperature. The reaction mixture was decomposed with water. The layers were separated. The aqueous phase was extracted with tetrahydrofuran. The combined organic layers were dried, filtered and evaporated. The residue was crystallized from acetonitrile. The product was filtered off and dried, yielding 18 parts (63.5%) of $N^5$-[(4-fluorophenyl)methyl]-4,5-pyrimidinediamine (interm. 12).

Following the same procedure and using equivalent amounts of the appropriate starting materials, there were also prepared:

N-(4-amino-6-hydroxy-5-pyrimidinyl)-4-fluorobenzamide (interm. 13); and
6-amino-5-[[(4-fluorophenyl)methyl]amino]-4-pyrimidinol (interm. 14).

Example 3

A mixture of 62.2 parts of 6-chloro-$N^4$-(2-pyridinylmethyl)-4,5-pyrimidinediamine, 3 parts of a solution of thiophene in methanol 4%, 20 parts of calcium oxide and 400 parts of methanol was hydrogenated at normal pressure and at 50° C. with 5 parts of palladium-on-charcoal catalyst 10%. After the calculated amount of hydrogen was taken up, the catalyst was filtered off and the filtrate was evaporated, yielding 63.5 parts (100%) of N$^4$-(2-pyridinylmethyl)-4,5-pyrimidinediamine as a residue (interim. 15).

In a similar manner there were also prepared:

N$^4$-[(4-fluorophenyl)methyl]-4,5-pyrimidinediamine as a residue (interim. 16);
N$^4$-(2-furanylmethyl)-4,5-pyrimidinediamine; mp. 116.4° C. (interim. 17);
N$^4$-(2-thienylmethyl)-4,5-pyrimidinediame (interim. 18);
N$^4$-[(5-methyl-2-furanyl)methyl]-4,5-pyrimidinediamine (interim. 19);
N$^4$-(2-pyrazinylmethyl)-4,5-pyrimidinediamine as a residue (interim. 20);
N$^4$-(4-methoxyphenyl)methyl]-4,5-pyrimidinediamine (interim. 21); and
N$^4$-(4-thiazolylmethyl)-4,5-pyrimidinediamine (interim. 22).

In a similar manner there is also prepared: N$^4$-[(2,4-dimethylphenyl)methyl]-4,5-pyrimidinediamine (interm. 23).

Example 4

A mixture of 8.72 parts of N$^4$-[(4-fluorophenyl)methyl]-4,5-pyrimidinediamine, 63 parts of carbon disulfide and 45 parts of N,N-dimethylformamide was stirred for 3 hours at reflux temperature. After cooling, the reaction mixture was poured into water. The precipitated product was filtered off and dried, yielding 10.1 parts (78.9%) of 9-[(4-fluorophenyl)methyl]-9H-purine-8-thiol (interm. 24).

To a stirred mixture of 4.6 parts of Potassium hydroxide and 200 parts of water were added portionwise 1.7 parts of iodomethane, followed by the dropwise addition of 3.8 parts of 9-[(4-fluorophenyl)methyl]-9H-purine-8-thiol. Upon complete addition, the whole was stirred for 2 hours at room temperature. The precipitated product was filtered off and dried, yielding 3.45 parts (73.9%) of 9-[(4-fluorophenyl)methyl]-8-(methylthio)-9H-purine; mp. 167.1° C. (interim. 25).

Example 5

A mixture of 26 parts of methyl 3-methyl-4-oxo-1-piperidinecarboxylate, 16.5 parts of benzenemethanamine, 2 parts of a solution of thiophene in ethanol 4% and 200 parts of methanol was hydrogenated at normal pressure and at room temperature with 3 parts of palladium-on-charcoal catalyst 10%. After the calculated amount of hydrogen was taken up, the catalyst was filtered off and the filtrate was evaporated to dry, yielding 40.2 parts of methyl 3-methyl-4-[(phenylmethyl)amino]-1-piperidinecarboxylate as a residue (interm. 26).

A mixture of 40 parts of methyl 3-methyl-4-[(phenylmethyl)amino]-1-piperidinecarboxylate and 160 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated to dry. The residue was distilled (bp. 80° C. at 0.1 mm. pressure). The distillate was further purified by gas-chromatography (at 215° C. and at 10 lbs/sq. inch), yielding 8.6 parts of methyl 4-amino-3-methyl-1-piperidinecarboxylate (interm. 27)

To a stirred and cooled (−10° C.) mixture of 138.6 parts of carbon disulfide, 113.8 parts of N,N'-methanetetraylbis[cyclohexanamine] and 450 parts of tetrahydrofuran were added dropwise 106 parts of methyl 4-amino-3-methyl-1-piperidinecarboxylate at this low temperature. The reaction mixture was allowed to attain room temperature. After stirring for 1 hour at room temperature, the mixture was evaporated and the residue was stirred in 2,2'-oxybispropane. The precipitate was filtered off and the filtrate was evaporated, yielding 141.1 parts (100%) of methyl cis-4-isothiocyanato-3-methyl-1-piperidinecarboxylate as a residue (interm. 28).

Following the same procedure and using equivalent amounts of the appropriate starting materials, there were also prepared:
methyl (cis+trans)-methyl 4-amino-3-methyl-1-piperidinecarboxylate; bp. 136°-140° C. (water-jet) (interm. 29): and
methyl (cis+trans)-4-isothiocyanato-3-methyl-1-piperidinecarboxylate as a residue (interm. 30).

Example 6

A mixture of 42.5 parts of N$^4$-(2-furanylmethyl)-4,5-pyrimidinediamine, 50.5 parts of ethyl 4-isothiocyanato-1-piperidinecarboxylate and 630 parts of tetrahydrofuran was stirred for 48 hours at reflux temperature. After cooling, the product was filtered off, washed with tetrahydrofuran and 1,1'-oxybisethane and dried, yielding 86.4 parts (96.2%) of ethyl 4-[[[[4-[(2-furanylmethyl)amino]-5-pyrimidinyl]amino]thioxomethyl]-amino]-1-piperidinecarboxylate (interm. 31).

In a similar manner there were also prepared:

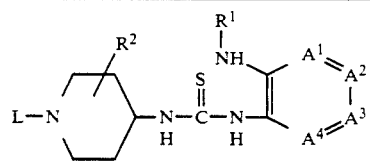

| No. | L | R$^2$ | R$^1$ | —A$^1$=A$^2$—A$^3$=A$^4$— | isomeric form | mp. °C. |
|---|---|---|---|---|---|---|
| 32 | C$_2$H$_5$OCO— | H | 4-F—C$_6$H$_4$—CH$_2$— | —N=C—N=C— | — | — |
| 33 | C$_2$H$_5$OCO— | H | 2-thienyl-CH$_2$— | —N=C—N=C— | — | — |
| 34 | C$_2$H$_5$OCO— | H | 2-pyridinyl-CH$_2$— | —N=C—N=C— | — | — |
| 35 | C$_6$H$_5$CH$_2$— | H | 4-F—C$_6$H$_4$—CH$_2$— | —C=N—C=N— | — | — |
| 36 | C$_2$H$_5$OCO— | H | (5-CH$_3$-2-furanyl)-CH$_2$— | —N=C—N=C— | — | — |
| 37 | C$_2$H$_5$OCO— | H | 2-pyrazinyl-CH$_2$— | —N=C—N=C— | — | — |
| 38 | CH$_3$OCO— | 3-CH$_3$ | 4-F—C$_6$H$_4$—CH$_2$— | —N=C—N=C— | cis | — |
| 39 | CH$_3$OCO— | 3-CH$_3$ | 4-F—C$_6$H$_4$—CH$_2$— | —N=C—N=C— | cis + trans | — |
| 40 | C$_2$H$_5$OCO— | H | 4-CH$_3$O—C$_6$H$_4$—CH$_2$— | —N=C—N=C— | — | — |

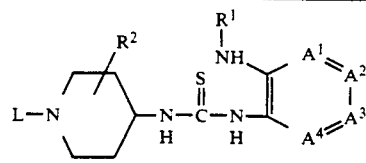

| No. | L | R² | R¹ | —A¹=A²—A³=A⁴— | isomeric form | mp. °C. |
|---|---|---|---|---|---|---|
| 41 | C₂H₅OCO— | H | 4-thiazolyl-CH₂— | —N=C—N=C— | — | — |

In a similar manner there were also prepared:

N-(4-amino-6-hydroxy-5-pyrimidinyl-N-[(4-fluorophenyl)methyl]-N'-[1-(phenylmethyl)-4-piperidinyl]-thiourea; mp. 192.9° C. (interm. 42); and ethyl 4-[[[(4-amino-6-hydroxy-5-pyrimidinyl)[(4-fluorophenyl)methyl]amino]-thioxomethyl]amino]-1-piperidinecarboxylate (interm. 43).

In a similar manner there is also prepared: ethyl 4-[[[4-[[(2,4-dimethylphenyl)methyl]amino]-5-pyrimidinyl]aminothioxomethyl]amino]-1-piperidinecarboxylate (interm. 44).

Example 7

A mixture of 52.4 parts of 1-(phenylmethyl)-4-piperidineacetic acid hydrochloride, 38.7 parts of N⁴-[(4-fluorophenyl)methyl]- 4,5-pyrimidinediamine and 765 parts of phosphoryl chloride was stirred and refluxed for 30 minutes. The reaction mixture was evaporated. The residue was decomposed with ice water. The product was extracted with dichloromethane after treatment with sodium hydroxide. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 37 parts (61%) of N-[4-[[(4-fluorophenyl)methyl]amino]-5-pyrimidinyl]-1-(phenylmethyl)-4-piperidineacetamide; mp. 157.3° C. (interm. 45).

Example 8

To a stirred mixture of 14.2 parts of isocyanatoethane, 29.2 parts of sodium azide and 135 parts of dry tetrahydrofuran was added a solution of 39 parts of aluminum chloride in 225 parts of dry tetrahydrofuran. Stirring was continued overnight at reflux temperature. The reaction mixture was cooled and acidified with a hydrochloric acid solution 6N. The whole was evaporated to dry and the product was extracted four times with 2-propanone. The combined extracts were dried, filtered and evaporated. The residue was dried overnight, yielding 18 parts (65%) of 1-ethyl-1,4-dihydro-5H-tetrazol-5-one (interm. 46).

To a stirred solution of 109 parts of 1,2-dibromoethane and 21.2 parts of sodium carbonate in 5 parts of water and 18 parts of N,N-dimethylformamide were added dropwise a solution of 22.5 parts of 1-ethyl-1,4-dihydro-5H-tetrazol-5-one in 5 parts of water and 27 parts of N,N-dimethylformamide at about 40° C. Upon completion, stirring was continued overnight at 40° C. The organic phase was separated, dried and distilled, yielding 9.8 parts (22%) of 1-(2-bromoethyl)-4-ethyl-1,4-dihydro-5H-tetrazol-5-one; bp. 110° C. at 0.1 mm pressure (interm. 47).

Example 9

A mixture of 50 parts of 2-thiazolamine, 76 parts of 3-acetyl-4,5-dihydro-2(3H)-furanone, 1.2 parts of concentrated hydrochloric acid and 270 parts of methylbenzene was stirred and refluxed for 2 hours using a water-separator. The reaction mixture was cooled and 340 parts of phosphoryl chloride were added at a temperature between 20° and 30° C. The whole was heated slowly to 100°~110° C. and stirring was continued for 2 hours at this temperature. The reaction mixture was evaporated and the residue was poured into a mixture of crushed ice and ammonium hydroxide. The product was extracted with trichloromethane. The extract was dried, filtered and evaporated. The residue was purified by column chromatography over silica gel using a mixture of trichloromethane and methanol (95:5 by volume) as eluent. The pure fractions were collected and the eluent was evaporated. The residue was crystallized from a mixture of 2-propanol and 1,1'-oxybisethane, yielding 36 parts of 6-(2-chloroethyl)-7-methyl-5H-thiazolo[3,2-a]pyrimidin-5-one (interm. 48).

B. Preparation of Final Compounds

Example 10

A mixture of 20.65 parts of 1-(phenylmethyl)-4-piperidineacetic acid hydrochloride, 19.5 parts of 6-chloro-N⁴-[(4-fluorophenyl)methyl]-4,5-pyrimidinediamine and 510 parts of phosphoryl chloride was stirred and refluxed for 13 hours. The reaction mixture was evaporated. The residue was poured into ice water. The whole was treated with sodium hydroxide. The product was extracted with 4-methyl-2-pentanone. The extract was washed with water, dried, filtered and evaporated. The residue was purified by column chromatography over silica gel using a mixture of trichloromethane and methanol, saturated with ammonia, (97:3 by volume) as eluent. The first fraction was collected and the eluent was evaporated, yielding 23.6 parts (75%) of 6-chloro-9-[(4-fluorophenyl)methyl]-8-[[1-(phenylmethyl)-4-piperidinyl]-methyl]-9H-purine as an oily residue (compound 1).

In a similar manner there was also prepared:

6-chloro-7-[(4-fluorophenyl)methyl]-8-[[1-(phenylmethyl)-4-piperidinyl]-methyl]-7H-purine (compound 2); and 9-(4-fluorophenyl)methyl]-6-methyl-8-[[1-(phenylmethyl)-4-piperidinyl]-methyl]-9H-purine as an oily residue (compound 3).

Example 11

A mixture of 36 parts of N-[4-[[(4-fluorophenyl)methyl]amino]-5-pyrimidinyl]-1-(phenylmethyl}-4-piperidineacetamide and 935 parts of phosphoryl chloride was stirred and refluxed for 8 hours. After cooling, the reaction mixture was evaporated. The residue was decomposed in ice water. The whole was treated with a sodium hydroxide solution. The product was extracted with 4-methyl-2-pentanone. The extract was dried, filtered and evaporated. The residue was purified by column chromatography over silica gel using a mixture of trichloromethane and methanol, saturated with ammonia, (97:3 by volume) as eluent. The pure fractions were collected and the eluent was evaporated. The residue was stirred in 2,2'-oxybispropane. The product was filtered off and crystallized from acetonitrile. The product was filtered off and dried, yielding 10.6 parts (30.4%) of 9-[(4-fluorophenyl)methyl]-8-[[1-(phenylmethyl)-4-piperidinyl]methyl]-9H-purine; mp. 136.4° C. (compound 4).

Example 12

A mixture of 12.6 parts of 1-(phenylmethyl)-4-piperidinol, 3.2 parts of a sodium hydride dispersion 50% and 200 parts of N,N-dimethylacetamide was stirred for 1 hour at room temperature. 18 Parts of 9-[(4-fluorophenyl)methyl]-8-(methYlthio)-9H-purine were added portionwise and upon completion, stirring was continued for 4 hours at room temperature. The reaction mixture was poured into water. The product was filtered off and taken up in trichloromethane. The organic layer was washed with water and filtered over diatomaceous earth. The filtrate was dried, filtered and evaporated. After crystallization from acetonitrile, the product was filtered off and dried, yielding 16.75 parts (61.1%) of 9-[(4-fluorophenyl)methyl]-8-[[1-(phenylmethyl)-4-piperidinyl]oxy]-9H-purine; mp. 117.0° C. (compound 5).

Example 13

To a stirred mixture of 13 parts of 9-[(4-fluorophenyl)methyl]-9H-purine-8-thiol and 300 parts of water were added 2 parts of sodium hydroxide. The reaction mixture was filtered over diatomaceous earth. After evaporation, the residue was taken up in methylbenzene and the solvent was evaporated again (this was repeated twice). The residue was taken up in 270 parts of N,N-dimethylacetamide and 19.3 parts of 1-[(4-methylphenyl)sulfonyl]-4-piperidinol methanesulfonate (ester) were added. The whole was stirred over weekend at 60° C. The reaction mixture was poured into water and the product was extracted with 4-methyl-2-pentanone. The extract was washed with water, dried, filtered and evaporated, yielding 27 parts (100%) of 4-[[9-[{4-fluorophenyl)methyl]-9H-purin-8-yl]thio]-1-[(4-methylphenyl)sulfonyl]piperidine (compound 6).

Example 14

A mixture of 4 parts of ethyl 4-[[[[4-[(2-furanylmethyl)amino]-5-pyrimidinyl]amino]thioxomethyl]amino]-1-piperidinecarboxylate, 6 parts of mercury(II)oxide and 80 parts of ethanol was stirred for 2 hours at reflux temperature. The whole was filtered while hot over Hyflo ® and the filtrate was evaporated. The residue was crystallized from a mixture of acetonitrile and ethanol. The product was filtered off and dried, yielding 0.8 parts (21.5%) of ethyl 4-[[9-(2-furanylmethyl)-9H-purin-8-yl]amino]-1-piperidinecarboxylate; mp. 171.9° C. (compound 7).

Following the same procedure and using equivalent amounts of the appropriate starting materials, there was also prepared: ethyl 4-[[9-[(4-fluorophenyl)methyl]-9H-purin-8-yl]amino]-1-piperidinecarboxylate; mp. 174.5° C. (compound 8).

Example 15

A mixture of 24 parts of ethyl 4-[[[[4-[(phenylmethyl)amino]-5-pyrimidinyl]amino]thioxomethyl]amino]-1-piperidinecarboxylate, 24 parts of mercury(II) oxide and 240 parts of methanol, saturated with ammonia was stirred overnight at reflux temperature. The reaction mixture was filtered while hot and the filtrate was evaporated. The residue was taken up in a mixture of trichloromethane and ethanol. After washing with water, the organic layer was evaporated and the residue was crystallized from acetonitrile. The product was filtered off and dried, yielding 20.3 parts (92.1%) of ethyl 4-[[9-(phenylmethyl)-9H-purin-8-yl]amino]-1-piperidinecarboxylate; mp. 156.9° C. (compound 9).

In a similar manner there were also prepared:

ethyl 4-[[9-(2-thienylmethyl)-9H-purin-8-yl]amino]-1-piperidinecarboxylate as a residue (compound 10);

ethyl 4-[[9-(2-pyridinylmethyl)-9H-purin-B-yl]amino]-1-piperidinecarboxylate (compound 11);

ethyl 4-[[9-[(5-methyl-2-furanyl)methyl]-9H-purin-8-yl]amino]-1-piperidine-carboxylate as a residue (compound 12);

ethyl 4-[[9-(2-pyrazinylmethyl)-9H-purin-8-yl]amino]-1-piperidinecarboxylate as a residue (compound 13);

ethyl 4-[(9-methyl-9H-purin-8-yl)amino]-1-piperidinecarboxylate; mp. 169.6° C. (compound 14);

ethyl 4-[[9-[(4-methoxyphenyl)methyl]-9H-purin-8-yl]amino]-1-piperidinecarboxylate; mp. 168.1° C. (compound 15); and N-[1-(phenylmethyl)-4-piperidinyl]-9H-purin-8-amine; mp. 276.1° C. (compound 16).

Example 16

A mixture of 15.7 parts of ethyl 4-[[[[4-(cyclopropylamino)-5-pyrimidinyl]amino]thioxomethyl]amino]-1-piperidinecarboxylate, 20 parts of mercury(II) oxide. 40 parts of ethanol and 135 parts of N,N-dimethylacetamide was stirred overnight at 80° C. The reaction mixture was filtered over diatomaceous earth while hot. The filtrate was poured into water and the product was extracted with dichloromethane. The organic layer was dried, filtered and evaporated. The residue was crystallized from acetonitrile. The product was filtered off and dried, yielding 2.2 parts (14.1%) of ethyl 4-[(9-cyclopropyl-9H-purin-8-Yl)amino]-1-piperidinecarboxylate; mp. 177.0° C. (compound 17).

In a similar manner there was also prepared: ethyl 4-[[9-(4-thiazolylmethyl)-9H-purin-8-yl]amino]-1-piperidinecarboxylate (compound 18).

Example 17

A mixture of 13 parts of methyl cis-4-[[[[4-[[(4-fluorophenyl)methyl]amino]-5-pyrimidinyl]amino]thioxomethyl]amino]-3-methyl-1-piperidinecarboxylate, 13 parts of mercury(II) oxide, 0.1 parts of sulfur and 160 parts of methanol, saturated with ammonia was stirred for 0.5 hours at reflux temperature. The reaction mixture was filtered over diatomaceous earth while hot and the filtrate was evaporated. The residue was poured into water and the product was extracted with trichloromethane. The extract was washed with water, dried, filtered and evaporated. The residue was solidified in 1,1'-oxybisethane. The product was filtered off and dried, yielding 7 parts (58.5%) of methyl cis-4-[[9-[(4-fluorophenyl)methyl]-9H-purin-8-yl]amino]-3-methyl-1-piperidinecarboxylate; mp. 152.2° C. (compound 19).

In a similar manner there were also prepared:

7-[(4-fluorophenyl)methyl]-N-[1-(phenylmethyl)-4-Piperidinyl]-7H-purin-8-amine; mp. 251.1° C. (compound 20).

methyl (cis+trans)-4-[[9-[(4-fluorophenyl)methyl]-9H-purin-8-yl]amino]-3-methyl-1-piperidinecarboxylate (compound 21);

In a similar manner there are also prepared:

ethyl 4-[[9-[(4-fluorophenyl)methyl]-9H-purin-8-yl]methylamino]-1-piperidinecarboxylate (compound 22); and ethyl 4-[[9-[(2,4-dimethylphenyl)methyl]-9H-purin-8-yl]amino]-1-piperidinecarboxylate (compound 23).

Example 18

A mixture of 88.8 parts of ethyl 4-[[[(4-amino-6-hydroxy-5-pyrimidinyl)[(4-fluorophenyl)methyl]amino]thioxomethyl]amino]-1-piperidinecarboxylate, 88 parts of mercury(II) oxide, 0.1 parts of sulfur and 1200 parts of ethanol was stirred overnight at reflux temperature. The reaction mixture was filtered over diatomaceous earth while hot and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was crystalized from ethyl acetate. The product was filtered off and dried, yielding 50.7 parts (66.1%) of ethyl 4-[[7-amino-1-[(4-fluorophenyl)methyl]oxazolo[5,4-d]-pyrimidin-2(1H)-yliden]amino]-1-piperidinecarboxylate; mp. 174.6° C. (compound 24).

A mixture of 50.7 parts of ethyl 4-[[7-amino-1-[(4-fluorophenyl)-methyl]oxazolo[5,4-d]pyrimidin-2(1H)-yliden]amino]-1-piperidinecarboxylate and 3050 parts of phosphoryl chloride was stirred for 90 minutes at reflux temperature. The reaction mixture was evaporated. The residue was poured into ice water. The whole was treated with ammonium hydroxide. The product was extracted with 4-methyl-2-pentanone. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 21.6 parts (41.5%) of ethyl 4-[[6-chloro-7-[(4-fluorophenyl)methyl]-7H-purin-8-yl]amino]-1-piperidinecarboxylate; mp. 126.6° C. (compound 25).

Following the same procedure and using equivalent amounts of the appropriate starting materials, there were also prepared:

1-[(4-fluorophenyl)methyl]-2,3-dihydro-2-[[1-(phenylmethyl)-4-piperidinyl]imino]oxazolo[5,4-d]-pyrimidine-4-amine; mp. 178.5° C. (compound 26): and 6-chloro-7-[(4-fluorophenyl)methyl]-N-[1-(phenylmethyl)-4-piperidinyl]-7H-purin-8-amine; mp. 248.6° C. (compound 27).

Example 19

A mixture of 16 parts of 6-chloro-7-[(4-fluorophenyl)-methyl]-8-[[1-(phenylmethyl)-4-piperidinyl]methyl]-7H-purine, 4.65 parts of ethyl carbonochloridate and 180 parts of methylbenzene was stirred for 2 hours at reflux temperature. After cooling, the reaction mixture was treated with ammonium hydroxide and the product was extracted with methylbenzene. The extract was washed with water, dried, filtered and evaporated, yielding 18.7 parts (100%) of ethyl 4-[[6-chloro-7-[(4-fluorophenyl)methyl]-7H-purin-8-yl]methyl]-1-piperidinecarboxylate as a residue (compound 28).

In a similar manner there was also prepared:

ethyl 4-[[9-[(4-fluorophenyl)methyl]-6-methyl-9H-Purin-8-Yl]-methyl]-1-piperidinecarboxylate (compound 29); and ethyl 4-[[6-chloro-9-[(4-fluorophenyl)methyl]-9H-purin-8-yl]-methyl]-1-piperidinecarboxylate as a residue (compound 30).

Example 20

7 A mixture of 24.8 parts of 4-[[9-[(4-fluorophenyl)-methyl]-9H-purin-8-yl]thio]-1-[(4-methylphenyl)sulfonyl]piperidine and 300 parts of acetic acid, saturated with hydrogen bromide was stirred overnight at room temperature. After evaporation, the residue was taken up in water. The whole was treated with a sodium hydroxide solution and extracted with dichloromethane. The extract was acidified with a hydrochloric acid solution and extracted with water. The aqueous layer was treated with a sodium hydroxide solution and the product was extracted with dichloromethane. The extract was washed with water, dried, filtered and evaporated. The residue was purified by column chromatography over silica gel using a mixture of trichloromethane and methanol. (95:5 by volume)→trichloromethane and methanol, saturated with ammonia, (90:10 by volume) as eluents. The pure fractions were collected and the eluent was evaporated. The residue was crystallized from acetonitrile. The product was filtered off and dried, yielding 3.0 parts (17.4%) of 9-[(4-fluorophenyl)-methyl]-8-(4-piperidinylthio)-9H-purine; mp. 113.5° C. (compound 31).

In a similar manner there is also prepared: 9-[(4-fluorophenyl)methyl]-8-(4-piperidinylsulfonyl)-9H-purine (compound 32).

Example 21

A mixture of 60.5 parts of ethyl 4-.[9-(2-furanylmethyl)-9H-purin-8-yl]amino]-1-piperidinecarboxylate, 90 parts of potassium hydroxide, 800 parts of 2-propanol and 20 parts of water was stirred for 48 hours at reflux temperature. The reaction mixture was evaporated. The reaction mixture was poured into water while stirring. The product was filtered off and dried, yielding a first fraction of 36.2 parts of 9-(2-furanylmethyl)-N-(4-Piperidinyl)-9H-purin-8-amine hemihydrate. The aqueous phase was extracted with dichloromethane. The organic layer was dried, filtered and evaporated. The oily residue was stirred in acetonitrile and 2,2'-oxybispropane. The product was filtered off and dried, yielding a second fraction of 5.6 parts of 9-(2-furanylmethyl)-N-(4-piperidinyl)-9H-purin-8-amine. Total yield 41.8 parts (86%) of 9-(2-furanylmethyl)-N-(4-piperidinyl)-9H-purin-8-amine hemihydrate; mp. 164.1° C. (compound 33).

Following the same procedure and using equivalent amounts of the appropriate starting materials, there were also prepared:

9-[(4-fluorophenyl)methyl]-N-(4-piperidinyl)-9H-purin-8-amine dihydrochloride; mp. 275.0° C. (compound 34);
N-(4-piperidinyl)-9-(2-thienylmethyl)-9H-purin-8-amine; mp. 189.6° C. (compound 35);
N-(4-piperidinyl)-9-(2-pyridinylmethyl)-9H-purin-8-amine; mp. 194.8° C. (compound 36);
9-[(5-methyl-2-furanyl)methyl]-N-(4-piperidinYl)-9H-Purin-8-amine; mp. 165.1° C. (compound 37);
N-(4-piperidinyl)-9-(2-pyrazinylmethyl)-9H-purin-8-amine as a residue (compound 38); and
9-[(4-methoxyphenyl)methyl]-N-(4-piperidinyl)-9H-purin-8-amine hemihydrate; mp. 144.1° C. (compound 39).

In a similar manner there is also prepared: 9-[(2.4-dimethylphenyl)methyl]-N-(4-piperidinyl)-9H-purin-8-amine (compound 40).

Example 22

A mixture of 7.5 Parts of ethyl 4-[[6-chloro-7-[(4-fluorophenyl)methyl]-7H-purin-8-yl]amino]-1-piperidinecarboxylate and 150 parts of a hydrobromic acid solution 48% in water was stirred overnight at 80° C. The reaction mixture was evaporated. The residue was stirred in 2-propanone. The product was filtered off and dried, yielding 8.5 parts (100%) of 7-[(4-fluorophenyl)methyl]-8-(4-piperidinylamino)-7H-purin-6-ol dihydrobromide as a residue (compound 41).

In a similar manner there were also prepared:
9-[(4-fluorophenyl)methyl]-8-(4-piperidinylmethyl)-9H-purin-6-ol dihydrobromide as a residue (compound 42); and
7-[(4-fluorophenyl)methyl]-8-(4-piperidinylmethyl)-7H-purin-6-ol dihydrobromide; mp. 277.8° C. (compound 43).

Example 23

A mixture of 10.5 parts of ethyl 4-[(9-methyl-9H-purin-8-Yl)amino]-1-piperidinecarboxylate and 300 parts of a hydrobromic acid solution 48% in water was stirred for 6 hours at 80° C. After evaporation, the residue was boiled in methanol. The reaction mixture was cooled and the precipitated product was filtered off, boiled in methanol again and yielded, after filtration and drying . 7.7 parts (56.6%) of 9-methyl-N-(4-piperidinyl)-9H-purin-8-amine dihydrobromide; mp. 298.3° C. (compound 44).

In a similar manner there were also prepared:
cis-9-[(4-fluorophenyl)methyl]-N-(3-methyl-4-Piperidinyl)-9H-purin-8-amine dihydrobromide (compound 45);
9-(phenylmethyl)-N-(4-piperidinyl)-9H-purin-8-amine dihydrobromide; mp. 270.9° C. (compound 46);
(cis+trans)-9-[(4-fluorophenyl)methyl]-N-(3-methyl-4-piPeridinYl)-9H-purin-8-amine dihydrobromide (compound 47);
9-[(4-fluorophenyl)methyl]-6-methyl-8-(4-piperidinyl)methyl)-9H-purine as a residue (compound 48);

9-cYclopropyl-N-(4-piperidinyl)-9H-purin-8-amine: mp 140.6° C. (compound 49); and
N-(4-piperidinyl)-9-(4-thiazolylmethyl)-9H-purin-8-amine: mp. 208.4° C. (compound 50).

In a similar manner there is also prepared: 9-[4-fluorophenyl)methyl]-N-methyl-N-(4-piperidinyl)-9H-purin 8-amine (compound 51).

A mixture of 17.6 parts of 9-[(4-fluorophenyl)methyl]-8-[[1-(phenylmethyl)-4-piperidinyl]methyl]-9H-purine and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in water. The product was extracted with trichloromethane. The extract was dried, filtered and evaporated. The residue was converted into the ethanedioate salt in ethanol. The salt was filtered off and dried, yielding 8.1 parts (38.1%) of 9-[(4-fluorophenyl)methyl]-8-(4-piperidinylmethyl)-9H-purine ethanedioate(1:2); mp. 163.9° C. (compound 52).

In a similar manner there were also prepared:
7-[(4-fluorophenyl)methyl]-N-(4-piperidinyl)]-7H-purin-8-amine as a residue (compound 53); and
9-[(4-fluorophenyl)methyl]-6-methoxy-8-(4-piperidinylmethyl)-9H-purine (compound 54).

Example 25

A mixture of 15 parts of 6-chloro-7-[(4-fluorophenyl)methyl]-8-[[1-(phenylmethyl)-4-piperidinyl]-methyl]-7H-purine. 5 parts of calcium oxide and 200 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in water. The product was extracted with dichloromethane. The extract was dried, filtered and evaporated. The residue was purified by column chromatography over silica gel using a mixture of trichloromethane and methanol, saturated with ammonia. (95:5→85:15 by volume) as eluent. The pure fractions were collected and the eluent was evaporated, yielding 5.8 parts (54%) of 7-[(4-fluorophenyl)methyl]-8-(4-piperidinylmethyl)-7H-purine as a residue (compound 55).

Example 26

A mixture of 16.25 parts of 9-[(4-fluorophenyl)methyl]-8-[[1-(phenylmethyl)-4-piperidinyl]oxy]-9H-purine and 200 parts of methanol was hydrogenated at normal pressure and at 50° C. with 3 parts of palladium-on-charcoal catalyst 10% and 6 parts of Raney-nickel catalyst. After the calculated amount of hydrogen was taken up, the catalyst was filtered off and the filtrate was evaporated. The residue was taken up in trichloromethane and water was added. The product was extracted with trichloromethane. The extract was washed with water, dried, filtered and evaporated. The residue was stirred in 1,1'-oxybisethane. The precipitated product was filtered off and dried, yielding 10.5 parts (82.2%) of 9-[(4-fluorophenyl)methyl]-8-(4-piperidinyloxy)-9H-purine; mp. 79.3° C. (compound 56).

Example 27

A mixture of 3.2 parts of 2,3-dihydro-1,4-benzodioxin-2-methanol 4-methylbenzenesulfonate(ester), 5 parts of 9-(4-fluorophenyl)methyl]-8-(4-piperidinylmethyl)-9H-purin-6-ol dihydrobromide, 3 parts of sodium carbonate and 45 parts of N,N-dimethylacetamide was stirred overnight at 70° C. After cooling, the reaction mixture was filtered over diatomaceous earth and the filtrate was evaporated. The residue was purified by column chromatography over silica gel using a mixture of trichloromethane and methanol, saturated with ammonia, (90:10 by volume) as eluent. The pure fractions were collected and the eluent was evaporated. The residue was crystallized twice: first from acetonitrile and then from ethanol. The product was filtered off and dried, yielding 0.8 parts (16.3%) of 8-[[1-[(2,3-dihydro-1,4-benzodioxin-2-yl)methyl]-4-piperidinyl]methyl]-9-[(4-fluorophenyl)methyl]-9H-purin-6-ol; mp. 200.7° C. (compound 57).

In a similar manner there was also prepared: 8-[[1-[(2,3-dihydro-1,4-benzodioxin-2-yl)methyl]-4-piperidinYl]amino]-7-[(4-fluorophenyl)methyl]-7H-purin-6-ol: mp. 257.5° C. (compound 58).

Example 28

A mixture of 3.2 parts of 2,3-dihydro-1,4-benzodioxin-2-methanol 4-methylbenzenesulfonate {ester}. 4.5 parts of 7-[(4-fluorophenyl)methyl]-8-(4-piperidinylmethyl)-7H-purin-6-ol dihydrobromide, 4 parts of sodium carbonate and 45 parts of N,N-dimethylformamide was stirred overnight at 70° C. After cooling, the reaction mixture was filtered over diatomaceous earth and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 1.5 parts (34%) of 8-[[1-[(2,3-dihydro-1,4-benzodioxin-2-yl)methyl]-4-piperidinyl]methyl]-7-[(4-fluorophenyl) methyl]-7H-purin-6-ol: mp. 175.2° C. (compound 59).

In a similar manner there were also prepared:
N-[1-[(2,3-dihydro-1,4-benzodioxin-2-yl)methyl]-4-piperidinyl]-9-(2 furanyl-methyl)-9H-purin-8-amine dihydrochloride dihydrate; mp. 174.4° C. (compound 60); and
N-[1-[(2,3-dihydro-1,4-benzodioxin-2-yl)methyl]-4-piperidinyl]-9-[(5-methyl-2-furanyl)methyl]-9H-purin-8-amine; mp. 200.8° C. (compound 61).

Example 29

A mixture of 1.9 parts of 1-(2-chloroethyl)-4-methoxybenzene, 5 parts of 7-[(4-fluorophenyl)methyl]-8-(4-piperidinylmethyl)-7H-purin-6-ol dihydrobromide, 4 parts of sodium carbonate and 45 parts of N,N-dimethylacetamide was stirred overnight at 70° C. After cooling, the reaction mixture was filtered over diatomaceous earth and the filtrate was evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetontrile. The product was filtered off and dried, yielding 2.2 parts (46%) of 7-[(4-fluorophenyl)methyl]-8-[[1-[2-(4-methoxyphenyl)ethyl]-4-piperidinyl]methyl]-7H-purin-6-ol; mp. 122.2° C. (compound 62).

In a similar manner there were also prepared:

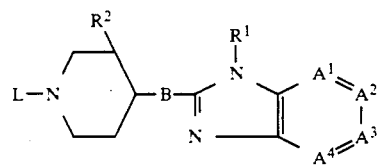

| No. | L | R² | B | R¹ | —A¹=A²—A³=A⁴— | isom. form | mp. °C. |
|---|---|---|---|---|---|---|---|
| 63 | 4-CH₃O—C₆H₄—C₂H₅— | H | CH₂ | 4-F—C₆H₄—CH₂— | —N=C—N=C(OH)— | — | 197.0 |
| 64 | 4-CH₃O—C₆H₄—C₂H₅— | H | O | 4-F—C₆H₄—CH₂— | —N=C—N=C— | — | 120.0 |
| 65 | 4-CH₃O—C₆H₄—C₂H₅— | CH₃ | NH | 4-F—C₆H₄—CH₂— | —N=C—N=C— | cis | 160.5 |
| 66 | 4-CH₃O—C₆H₄—C₂H₅— | H | NH | CH₃— | —N=C—N=C— | — | 136.5 |
| 67 | 4-CH₃O—C₆H₄—CH₂— | H | NH | 4-F—C₆H₄—CH₂— | —C=N—C=N— | — | 216.0 |
| 68 | 4-CH₃O—C₆H₄—C₂H₅— | H | NH | cyclopropyl- | —N=C—N=C— | — | 166.1 |
| 69 | 4-CH₃O—C₆H₄—C₂H₅— | H | NH | 4-thiazolyl-CH₂— | —N=C—N=C— | — | 152.2 |
| 70 | 4-CH₃O—C₆H₄—C₂H₅— | H | NH | 4-CH₃O—C₆H₄—CH₂— | —N=C—N=C— | — | 167.8 |
| 71 | 4-CH₃O—C₆H₄—C₂H₅— | H | S | 4-F—C₆H₄—CH₂— | —N=C—N=C— | — | 102.0 |

In a similar manner there are also prepared:

9-[(4-fluorophenyl)methyl]-8-[[1-[2-(2-methoxyphenyl)ethyl]-4-piperidinyl]methyl]-9H-purine (compound 72).

9-[(4-fluorophenyl)methyl]-N-methyl-N-[1-[2-(4-methoxyphenyl)ethyl]-4-piperidinyl]-9H-purin-8-amine (compound 73).

Example 30

A mixture of 2 parts of 1-(2-chloroethyl)-4-methoxybenzene, 3.1 parts of N-(4-piperidinyl)-9-(2-pyridinylmethyl)-9H-purin-8-amine, 1.5 parts of sodium carbonate and 45 parts of N,N-dimethylformamide was stirred overnight at 70° C. The reaction mixture was poured into water. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 2.2 parts (50%) of N-[1-[2-(4-methoxyphenyl)ethyl]-4-piperidinyl]-9-(2-pyridinylmethyl)-9H-purin-8-amine; mp. 144.5° C. (compound 74).

thylacetamide was stirred and heated overnight at 90° C. The reaction mixture was poured into water. The

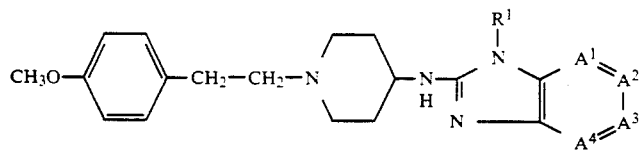

| No. | R¹ | —A¹=A²—A³=A⁴— | Base or salt form | mp. °C. |
|---|---|---|---|---|
| 75 | 4-F—C₆H₄—CH₂— | —N=C—N=C— | base | 170.6 |
| 76 | 2-furanyl-CH₂— | —N=C—N=C— | base | 140.6 |
| 77 | 2-thienyl-CH₂— | —N=C—N=C— | hemihydrate | 135.9 |
| 78 | 4-F—C₆H₄—CH₂— | —C=N—C=N— | base | 194.9 |
| 79 | 5-CH₃-2-furanyl-CH₂— | —N=C—N=C— | base | 164.9 |
| 80 | 4-F—C₆H₄—CH₂— | —N=C—N=C— | (E)-2-butenedioate(2:3) | 156.2 |
| 81 | 4-F—C₆H₄—CH₂— | —C=N—C=N— | base | 139.1 |
| 82 | 4-F—C₆H₄—CH₂— | —C(OH)=N—C=N— | monohydrate | 222.4 |
| 83 | C₆H₅—CH₂— | —N=C—N=C— | base | 161.5 |
| 84 | 4-F—C₆H₄—CH₂— | —N=C—N=C(CH₃)— | (E)-2-butenedioate(1:2) | 148.0 |

In a similar manner there was also prepared: ethyl [2-[4-[[9-(2-thienylmethyl)-9H-purin-8-yl]amino]-1-piperidinyl]ethyl]carbamate as a residue (compound 85).

In a similar manner there is also prepared: 9-[(4-fluorophenyl)methyl]-B-[[1-[2-(4-methoxyphenyl)ethyl]-4-Piperidinyl]sulfonyl]-9H-Purine (E)-2-butenedioate(1:2) (compound 86).

Example 31

A mixture of 1.45 parts of 3-(2-chloroethyl)-2-methyl-4H-pyrido-[1,2-a]pyrimidin-4-one, 2 parts of N-(4-piperidinyl)-9-(2-pyrazinylmethyl)-9H-purin-8-amine, 1 part of sodium carbonate and 45 parts of N,N-dimethylacetamide product was extracted with trichloromethane. The extract was dried, filtered and evaporated. The residue was purified by column chromatography over silica gel using a mixture of trichloromethane and methanol. saturated with ammonia, (95:5 by volume) as eluent. The pure fractions were collected and the eluent was evaporated. The residue was crystallized from acetonitrile. The product was filtered off and dried, yielding 0.9 parts (31.6%) of 2-methyl-3-[2-[4-[[9-(2-pyrazinylmethyl)-9H-purin-8-yl]amino]-1-piperidinyl]-ethyl]-4H-pyrido[1,2-a]pyrimidin-4-one; mp. 180.1° C. (compound 87).

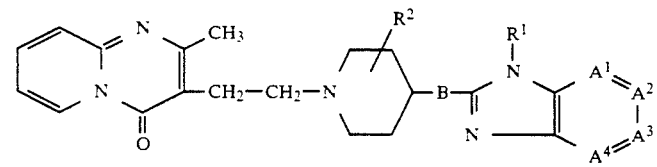

| No. | B | R¹ | R² | —A¹=A²—A³=A⁴— | Base or Salt form | mp. °C. |
|---|---|---|---|---|---|---|
| 88 | NH | 2-furanyl-CH₂— | H | —N=C—N=C— | H₂O | 176.6 |
| 89 | NH | 2-furanyl-CH₂— | H | —N=C—N=C— | base | 194.3 |
| 90 | NH | 2-pyridinyl-CH₂— | H | —N=C—N=C— | base | 201.3 |
| 91 | NH | 5-CH₃-2-furanyl-CH₂— | H | —N=C—N=C— | base | 208.1 |
| 92 | CH₂ | 4-F—C₆H₄—CH₂— | H | —N=C—N=C— | (E)-2-butenedioate (2:5) | 180.0 |
| 93 | NH | 4-F—C₆H₄—CH₂— | H | —C=N—C=N— | base | 211.5 |
| 94 | CH₂ | 4-F—C₆H₄—CH₂— | H | —C=N—C=N— | 3HCl.2H₂O | 217.5 |
| 95 | CH₂ | 4-F—C₆H₄—CH₂— | H | —N=C—N=C(OH)— | ½ H₂O | 196.5 |
| 96 | NH | 4-F—C₆H₄—CH₂— | H | —C(OH)=N—C=N— | H₂O | 201.9 |
| 97 | CH₂ | 4-F—C₆H₄—CH₂— | H | —C(OH)=N—C=N— | base | 210.1 |
| 98 | O | 4-F—C₆H₄—CH₂— | H | —N=C—N=C— | base | 152.4 |
| 99 | NH | CH₃— | H | —N=C—N=C— | ½ H₂O | 213.0 |
| 100 | NH | C₆H₅—CH₂— | H | —N=C—N=C— | base | 239.2 |
| 101 | NH | 4-F—C₆H₄—CH₂— | 3-CH₃ | —N=C—N=C— | base/cis + trans | 212.5 |
| 102 | NH | 4-F—C₆H₄—CH₂— | H | —N=C—N=C(CH₃)— | base | 148.9 |
| 103 | NH | 4-thiazolyl-CH₂— | H | —N=C—N=C— | base | 222.0 |

In a similar manner there were also prepared:

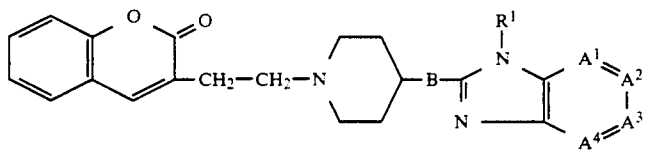

| No. | B | R$^1$ | —A$^1$=A$^2$—A$^3$=A$^4$— | Base or salt form | mp. °C. |
|---|---|---|---|---|---|
| 104 | NH | 2-furanyl-CH$_2$— | —N=C—N=C— | base | 181.6 |
| 105 | NH | 2-thienyl-CH$_2$— | —N=C—N=C— | H$_2$O | 168.2 |
| 106 | NH | 2-pyridinyl-CH$_2$— | —N=C—N=C— | H$_2$O | 164.7 |
| 107 | NH | 5-CH$_3$-2-furanyl-CH$_2$— | —N=C—N=C— | base | 173.4 |

In a similar manner there were also prepared:

3-[2-[4-[[9-[(4-fluorophenyl)methyl]-6-hydroxy-9H-purin-8-yl]-methyl]-1-piperidinyl]ethyl]-6,7,8,9-tetrahydro-2-methyl-4H-pyrido-[1,2-a]pyrimidin-4-one; mp. 171.1° C. (compound 108);

1-[3-[4-[[9-[(4-fluorophenyl)methyl]-6-methoxy-9H-purin-8-yl]methyl]-1-piperidinyl]propyl]-1,3-dihydro-2H-benzimidazol-2-one (E)-2-butenedioate(2:3); mp. 179.9° C. (compound 109);

9-[(4-fluorophenyl)methyl]-N-[1-[2-(4-morpholinyl)ethyl]-4-piperidinyl]-9H-purin-8-amine: mp 176.8° C. (compound 110);

7-methyl-6-[2-[4-[[9-(2-thienylmethyl)-9H-purin-8-yl]amino]-1-piperidinyl]ethyl]-5H-thiazolo[3,2-a]pyrimidin-5-one hemihydrate; mp. 104.5° C. (compound 111):

1-ethyl-4-[2-[4-[[9-[(4-fluorophenyl)methyl]-9H-purin-8-yl]amino]-1-piperidinyl]ethyl]-1,4-dihydro-5H-tetrazol-5-one: mp. 160.3° C. (compound 112); and 3-[2-[4-[[9-[(4-fluorophenyl)methyl]-9H-purin-8-yl]amino]-1-piperidinyl]ethyl]-2,4-(1H, 3H)quinazolinedione; mp. 241.0° C. (compound 113).

Example 32

A mixture of 1.8 parts of 1-(3-chloropropyl)-1,3-dihydro-2H-benzimidazol-2-one, 2.7 parts of 9-[(4-fluorophenyl)methyl]-8-(4-piperidinylmethyl)-9H-purine, 1 part of sodium carbonate and 45 parts of N,N-dimethylformamide was stirred and heated overnight at 70° C. After cooling, the reaction mixture was poured into water. The product was extracted with trichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in ethanol. The salt was filtered off and dried, yielding 2.85 parts (45.9%) of 1-[3-[4-[[9-[(4-fluorophenyl)methyl]-9H-purin-8-yl]methyl]-1-piperidinyl]-propyl]-1,3-dihydro-2H-benzimidazol-2-one (E)-2-butenedioate(1:2); mp. 186.2° C. (compound 114).

In a similar manner there were also prepared:

1-[2-[4-[[9-[(4-fluorophenyl)methyl]-9H-purin-8-yl]amino]-1-piperidinyl]-ethyl]-1,3-dihydro-2H-benzimidazol-2-one; mp. 242.4° C. (compound 115);

1-[3-[4-[[9-[(4-fluorophenyl)methyl]-6-hydroxy-9H-purin-8-yl]methyl]-1-piperidinyl]propyl]-1,3-dihydro-2H-benzimidazol-2-one; mp. 245.8° C. (compound 116).

In a similar manner there are also prepared:

3,7-dimethyl-6-[2-[4-[[9-[(4-fluorophenyl)methyl]-9H-purin-8-yl]-methyl]-1-piperidinyl]ethyl]-5H-thiazolo[3,2-a]pyrimidin-5-one (compound 117):

3-[2-[4-[[9-[(4-fluorophenyl)methyl]-9H-purin-8-yl]thio]-1-piperidinyl]ethyl]-2-methyl-4H-pyrido[1,2-a]pyrimidin-4-one (compound 118);

3-[2-[4-[[9-[(4-fluorophenyl)methyl]-9H-purin-8-yl]sulfonyl]-1-piperidinyl]ethyl]-2-methyl-4H-pyrido[1,2-a]pyrimidin-4-one (compound 119).

Example 33

A mixture of 1.2 parts of bromo-1-propene, 3.26 parts of 9-[(4-fluorophenyl)methyl]-N-(4-piperidinyl)-9H-purin-8-amine, 1.5 parts of sodium hydrogen carbonate and 40 parts of ethanol was stirred for 1 hour at reflux temperature. The reaction mixture was filtered over diatomaceous earth while hot and the filtrate was evaporated. The residue was taken up in water and the product was extracted with 4-methyl-2-pentanone. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 0.8 parts (22%) of 9-[(4-fluorophenyl)methyl]-N-[1-(2-propenyl)-4-piperidinyl]-9H-purin-8-amine; mp. 144.8° C. (compound 120).

In a similar manner there was also prepared:
4-[[9-[(4-fluorophenyl)methyl]-9H-purin-8-yl]amino]-N-(1-methylethyl)-1-piperidinepropanamide (E)-2-butenedioate(1:2); mp. 202.5° C. (compound 121).

Example 34

A mixture of 3.46 parts of N-(dihydro-3,3-diphenyl-2(3H)-furanylidene)-N-methylmethanaminium bromide, 3.1 parts of N-(4-piperidinyl)-9-(2-pyridinylmethyl)-9H-purin-8-amine, 1.5 parts of sodium carbonate and 45 parts of N,N-dimethylacetamide was stirred overnight at 80° C. After cooling, the reaction mixture was poured into water and the product was extracted with 4-methyl-2-pentanone. The extract was dried, filtered and evaporated. The residue was purified by column chromatography over silica gel using a mixture of trichloromethane and methanol, saturated with ammonia (95:5 by volume) as eluent. The pure fractions were collected and the eluent was evaporated. The residue was crystallized from acetonitrile. The product was filtered off and dried, yielding 4.1 parts (71%) of N,N- dimethyl-αα-diphenyl-4-[[9-(2-pyridinylmethyl)-9H-purin-8-yl]amino]-1-piperidinebutanamide; mp. 191.6° C. (compound 122).

Example 36

A mixture of 3 parts of poly(oxymethylene), 5 parts

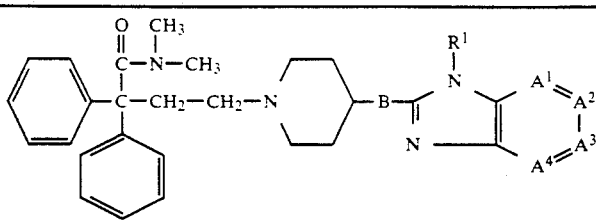

| No. | B | R¹ | —A¹=A²—A³=A⁴— | Base or salt form | mp. °C. |
|---|---|---|---|---|---|
| 123 | NH | 5-CH₃-2-furanyl-CH₂ | —N=C—N=C— | ½ H₂O | 87.5 |
| 124 | NH | C₆H₅—CH₂— | —N=C—N=C— | base | 204.2 |
| 125 | NH | 2-furanyl-CH₂— | —N=C—N=C— | base | 201.5 |
| 126 | CH₂ | 4-F—C₆H₄—CH₂— | —N=C—N=C(OH)— | base | 139.2 |
| 127 | NH | 2-thienyl-CH₂— | —N=C—N=C— | base | 197.7 |
| 128 | NH | 4-F—C₆H₄—CH₂— | —N=C—N=C— | 2HCl | 208.6 |
| 129 | NH | cyclopropyl | —N=C—N=C— | (E)-2-butendioate (2:5) | 172 |
| 130 | NH | 4-CH₃O—C₆H₄—CH₂— | —N=C—N=C— | (E)-2-butendioate (2:5) | 132.3 |

In a similar manner there were also prepared:

N,N,γ-trimethyl-α,α-diphenyl-4-[[9-(2-pyridinylmethyl)-9H-purin-8-yl]amino]-1-piperidinebutanamide; mp. 143.0° C. (compound 131);

4-[(9-methyl-9H-purin-8-yl)amino]-N,N-dimethyl-α,α-diphenyl-1-piperidinebutanamide (compound 132);

γN,N-trimethyl-4-[[9-(2-pyridinylmethyl)-9H-purin-8-yl]methyl-α,α-diphenyl-1-piperidinebutanamide (compound 133);

4-[[9-(2-furanylmethyl)-9H-purin-8-yl]amino]-γ,N,N-trimethyl-α,α-diphenyl-1-piperidinebutanamide (compound 134); and γ,N,N-trimethyl-4-[[9-[(5-methyl-2-furanyl)methyl]-9H-purin-8-yl]-amino]-α,α-diphenyl-1-piperidinebutanamide (compound 135).

In a similar manner there are also prepared:

β,N,N-trimethyl-4-[[9-(2-pyridinylmethyl)-9H-purin-8-yl]amino]-α,α-diphenyl-1-piperidinebutanamide (compound 136); and 4-[[9-[(4-fluorophenyl)methyl]-N,N-dimethyl-α,α-diphenyl-9H-purin-8-yl]oxy]-1-piperidinebutanamide (compound 137).

Example 35

A mixture of 4.9 parts of 9-[(4-fluorophenyl)methyl]-N-(4-piperidinyl)-9H-purin-8-amine, 1 part of a solution of thiopene in methanol 4%. 120 parts of methanol and 8 parts of 2-propanone was hydrogenated at normal pressure and at room temperature with 2 parts of palladium-on-charcoal catalyst 10%. After the calculated amount of hydrogen was taken up, the catalyst was filtered off and the filtrate was evaporated. The residue was purified by column chromatography over silica gel using a mixture of trichloromethane and methanol (90:10 by volume) as eluent. The pure fractions were collected and the eluent was evaporated. The residue was crystallized from acetonitrile, yielding 1.5 parts (27.2%) of 9-[(4-fluorophenyl)methyl]-N-[1-(1-methylethyl)-4-piperidinyl]-9H-purin-8-amine; mp. 185.6° C. (compound 138).

of 7-[(4-fluorophenyl)methyl]-8-(4-piperidinylamino)-7H-purin-6-ol dihydrobromide, 1 part of a solution of thiophene in methanol 4%, 5 parts of potassium acetate and 120 parts of methanol was hydrogenated at normal pressure and at room temperature with 2 parts of palladium-on-charcoal catalyst 10%. After the calculated amount of hydrogen was taken up, the catalyst was filtered off and the filtrate was evaporated. The residue was taken up in water and the whole was treated with sodium carbonate. The product was extracted with dichloromethane. The extract was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was crystallized from acetonitrile. The product was filtered off and dried, yielding 2 parts (56%) of 7-[(4-fluorophenyl)methyl]-8-[(1-methyl-4-piperidinyl)amino]-7H-purin-6-ol; mp. 255.6° C. (compound 139).

In a similar manner there was also prepared:

9-[(4-fluorophenyl)methyl]-8-[(1-methyl-4-piperidinyl)-methyl]-9H-purin-6-ol mp. 219.0° C. (compound 140).

Example 37

A mixture of 1.93 parts of 2-ethenylpyridine, 5 parts of 9-[(4-fluorophenyl)methyl]-N-(4-piperidinyl)-9H-purin-8-amine and 80 parts of 1-butanol was stirred and refluxed overnight. The reaction mixture was evaporated. The residue was purified by column chromatography over silica gel using first a mixture of trichloromethane and methanol (95:5 by volume) and then a mixture of trichloromethane and methanol, saturated with ammonia (95:5 by volume) as eluent. The pure fractions were collected and the eluent was evaporated. The residue was crystallized from acetonitrile, yielding 1 part (15%) of 9-[(4-fluorophenyl)methyl]-N-[1-[2-(2-pyridinyl)ethyl]-4-piperidinyl]-9H-purin-8-amine; mp. 172.3° C. (compound 141).

In a similar manner there were also prepared:

9-(2-furanylmethyl)-N-[1-[2-(2-pyridinyl)ethyl]-4-piperidinyl]-9H-purin-8-amine; mp. 144.5° C. (compound 142);

N-[1-[2-(2-pyridinyl)ethyl]-4-piperidinyl]-9-(2-thienylmethyl)-9H-purin-8-amine; mp. 152.7° C. (compound 143);

N-[1-[2-(2-pyridinyl)ethyl]-4-piperidinyl]-9-(2-pyridinylmethyl)-9H-purin-8-amine; mp. 163.8° C. (compound 144); and 9-[(5-methyl-2-furanyl)methyl]-N-[1-[2-(2-pyridinyl)ethyl]-4-piperidinyl]-9H-purin-8-amine; mp 163.2° C. (compound 145).

Example 38

During 30 minutes, gaseous oxirane was bubbled through a stirred mixture of 5 parts of 9-[(4-fluorophenyl)methyl]-N-(4-piperidinyl)-9H-purin-8-amine and 80 parts of methanol at room temperature. After stirring for 3 hours at room temperature, the reaction mixture was evaporated. The residue was purified by column chromatography over silica gel using a mixture of trichloromethane and methanol saturated with ammonia, (95:5 by volume) as eluent. The pure fractions were collected and the eluent was evaporated. The residue was crystallized from acetonitrile, yielding 2.2 parts (40%) of 4-[[9-[(4-fluorophenyl)methyl]-9H-purin-8-yl]amino]-1-piperidine-ethanol; mp. 158.7° C. (compound 146).

Example 39

A mixture of 3.22 parts of 2-chloroacetonitrile, 16 parts of 9-[(4-fluorophenyl)methyl]-N-(4-piperidinyl)-9H-purin-8-amine, 12.7 parts of sodium carbonate and 225 parts of N,N-dimethylformamide was stirred for 6 hours at room temperature. The reaction mixture was poured onto water. The product was extracted twice with trichloromethane. The combined extracts were dried, filtered and evaporated. The residue was crystallized from acetonitrile. The precipitate was filtered off and the filtrate was evaporated, yielding 16 parts of 4-[[9-[(4-fluorophenyl)methyl]-9H-purin-8-yl]amino]-1-piperidineacetonitrile as a residue (compound 147).

In a similar manner there were also prepared:

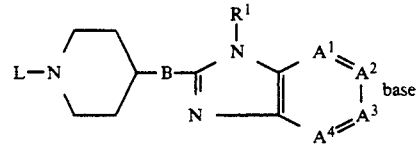

| No. | L | R$^1$ | B | —A$^1$=A$^2$—A$^3$=A$^4$— | mp. °C. |
|---|---|---|---|---|---|
| 148 | NC—CH$_2$— | 2-furanyl-CH$_2$— | NH | —N=C—N=C— | — |
| 149 | NC—(CH$_2$)$_4$— | 2-furanyl-CH$_2$— | NH | —N=C—N=C— | — |
| 150 | NC—CH$_2$— | 2-pyridinyl-CH$_2$— | NH | —N=C—N=C— | — |
| 151 | NC—CH$_2$— | 5-CH$_3$-2-furanyl-CH$_2$— | NH | —N=C—N=C— | — |
| 152 | NC—CH$_2$— | 4-F—C$_6$H$_4$—CH$_2$— | CH$_2$ | —N=C—N=C(OCH$_3$)— | — |
| 153 | NC—CH$_2$— | 4-F—C$_6$H$_4$—CH$_2$— | CH$_2$ | —N=C—N=C(OH)— | — |
| 154 | NC—CH$_2$— | 4-F—C$_6$H$_4$—CH$_2$— | CH$_2$ | —N=C—N=C— | — |

Example 40

A mixture of 18.2 parts of 4-[[9-[(4-fluorophenyl)methyl]-9H-purin-8-yl]amino]-1-piperidineacetonitrile and 240 parts of methanol saturated with ammonia was hydrogenated at normal pressure and at a temperature below 20° C. with 3 parts of Raney-nickel catalyst. After the calculated amount of hydrogen was taken up, the catalyst was filtered off and the filtrate was evaporated. The residue was crystallized from acetonitrile. The product was filtered off and dried, yielding 16 parts (87.5%) of N-[1-(2-aminoethyl)-4-piperidinyl]-9-[(4-fluorophenyl)methyl]-9H-purin-8-amine; mp. 146.1° C. (compound 155).

In a similar manner there were also prepared:

| No. | L | R$^1$ | B | —A$^1$=A$^2$—A$^3$=A$^4$— | mp. °C. |
|---|---|---|---|---|---|
| 156 | NH$_2$—(CH$_2$)$_2$— | 2-furanyl-CH$_2$— | NH | —N=C—N=C— | — |
| 157 | NH$_2$—(CH$_2$)$_5$— | 2-furanyl-CH$_2$— | NH | —N=C—N=C— | — |
| 158 | NH$_2$—(CH$_2$)$_2$— | 2-pyridinyl-CH$_2$— | NH | —N=C—N=C— | — |
| 159 | NH$_2$—(CH$_2$)$_2$— | 5-CH$_3$-2-furanyl-CH$_2$— | NH | —N=C—N=C— | — |
| 160 | NH$_2$—(CH$_2$)$_2$— | 4-F—C$_6$H$_4$—CH$_2$— | CH$_2$ | —N=C—N=C(OCH$_3$)— | — |
| 161 | NH$_2$—(CH$_2$)$_2$— | 4-F—C$_6$H$_4$—CH$_2$— | CH$_2$ | —N=C—N=C(OH)— | — |
| 162 | NH$_2$—(CH$_2$)$_2$— | 4-F—C$_6$H$_4$—CH$_2$— | CH$_2$ | —N=C—N=C— | — |

Example 41

A mixture of 10 parts of ethyl [2-[4-[[9-(2-thienylmethyl)-9H-purin-8-yl]amino]-1-piperidinyl]ethyl]carbamate, 10 parts of potassium hydroxide and 240 parts of 2-propanol was stirred overnight at reflux temperature. The reaction mixture was evaporated. Water was added. After stirring, the product was filtered off and dried, yielding 3.6 parts (56%) of N-[1-(2-aminoethyl)-4-piperidinyl]-9-(2-thienylmethyl)-9H-purin-8-amine (compound 163).

Example 42

A mixture of 1.7 parts of 2-chloropyrimidine, 5.5 parts of N-[1-(2 aminoethyl)-4-piperidinyl]-9-[(4-fluorophenyl)methyl]-9H-purin-8-amine, 1.5 parts of sodium hydrogen carbonate and 160 parts of ethanol was stirred and refluxed for 20 hours. The reaction mixture was evaporated. The residue was purified by column chromatography over silica gel using a mixture of trichloromethane and methanol (95:5 by volume) as eluent. The pure fractions were collected and the eluent was evaporated. The residue was crystallized from acetonitrile, yielding 4.5 parts (67%) of 9-[(4-fluorophenyl)methyl]-N-[1-[2-(2-pyrimidinylamino)ethyl]-4-piperidinyl]-9H-purin-8-amine; mp. 164.1° C. (compound 164).

ane was stirred for 2 hours at room temperature. A solution of 3.7 parts of N-[1-(2-aminoethyl)-4-piperidinyl]-9-[(4-fluorophenyl)methyl]-9H-purin-8-amine in dichloromethane was added and stirring was continued overnight at room temperature. The reaction mixture was washed with water. The separated organic layer was dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in a mixture of ethanol, 2-propanol and acetonitrile. The salt was filtered off and dried, yielding 2 parts (29%) of N-[2-[4-[[9-[(4-fluorophenyl)methyl]-9H-

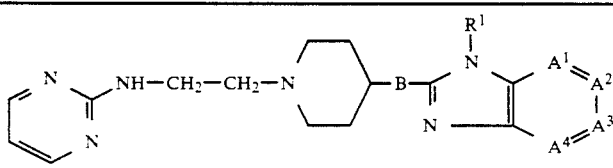

| No. | R¹ | B | —A¹=A²—A³=A⁴— | base or salt form | mp °C. |
|---|---|---|---|---|---|
| 165 | 2-furanyl-CH₂— | NH | —N=C—N=C— | base | 135.5 |
| 166 | 2-pyridinyl-CH₂— | NH | —N=C—N=C— | base | 140.1 |
| 167 | 2-thienyl-CH₂— | NH | —N=C—N=C— | base | 157.2 |
| 168 | 5-CH₃-2-furanyl-CH₂— | NH | —N=C—N=C— | base | 174.1 |
| 169 | 4-F—C₆H₄—CH₂— | CH₂ | —N=C—N=C(OCH₃)— | base | 138.1 |
| 170 | 4-F—C₆H₄—CH₂— | CH₂ | —N=C—N=C(OH)— | base | 212.9 |
| 171 | 4-F—C₆H₄—CH₂— | CH₂ | —N=C—N=C— | ethanedioate (1:3) | 102.1 |

Example 43

A mixture of 3.3 parts of 2-bromothiazole, 5.55 parts of N-[1-(2-aminoethyl)-4-piperidinyl]-9-[(4-fluorophenyl)methyl]-9H-purin-8-amine, 2.12 parts of sodium carbonate and 18 parts of N,N-dimethylacetamide was stirred and heated for 20 hours at 130° C. After cooling, the reaction mixture was poured onto water and the product was extracted with 4-methyl-2-pentanone. The extract was dried, filtered and evaporated. The residue was purified by column chromatography over silica gel using a mixture of trichloromethane, methanol and methanol saturated with ammonia, (90:5:5 by volume) as eluent. The pure fractions were collected and the eluent was evaporated. The residue was crystallized from acetonitrile. The product was filtered off and dried in high vacuo at 100° C., yielding 1.8 parts (26.5%) of 9-[(4-fluorophenyl)methyl]-N-[1-[2-(2-thiazolylamino)ethyl)-4-piperidinyl]-9H-purin-8-amine; mp. 165.4° C. (compound 172).

In a similar manner there was also prepared:

9-(2-furanylmethyl)-N-[1-[5-[(2-thiazolyl)amino]pentyl]-4-piperidinyl]-9H-purin-8-amine; mp. 167.4° C. (compound 173).

In a similar manner there is also prepared:

N²-[2-[4-[[9-(2-pyridinylmethyl)-9H-purin-8-yl]amino]-1-piperidinyl]ethyl]-1,3,4-thiadiazole-2,5-diamine (compound 174).

Example 44

A mixture of 1.1 parts of 3-furancarboxylic acid, 2.55 parts of 2-chloro-1-methylpyridinium iodide, 2 parts of N,N-diethylethanamine and 360 parts of dichloromethane purin-8-yl]amino]-1-piperidinyl]ethyl]-3-furancarboxamide (E)-2-butenedioate(1:2); mp. 132.2° C. (compound 175).

In a similar manner there were also prepared:

N-[2-[4-[[9-[(4-fluorophenyl)methyl]-9H-purin-8-yl]amino]-1-piperidinyl]ethyl]-2-thiophenecarboxamide (E)-2-butenedioate (1:2) monohydrate; mp. 135.7° C. (compound 176); and N-[2-[4-[[9-[(4-fluorophenyl)methyl]-9H-purin-8-yl]amino]-1-piperidinyl]ethyl]-2-thiazolecarboxamide (E)-2-butenedioate (1:2); mp. 184.0° C. (compound 177).

Example 45

A mixture of 1.4 parts of 2H-3,1-benzoxazine-2,4-(1H)-dione, 3.7 parts of N-[1-(2-aminoethyl)-4-piperidinyl]-9-[(4-fluorophenyl)methyl]-9H-purin-8-amine and 45 parts of N,N-dimethylformamide was stirred for 4 hours at 70° C. After cooling, the reaction mixture was poured into water and the product was extracted with 4-methyl-2-pentanone. The extract was washed with water, dried, filtered and evaporated. The residue was purified by column chromatography over silica gel using a mixture of trichloromethane and methanol, saturated with ammonia, (95:5 by volume) as eluent. The pure fractions were collected and the eluent was evaporated. The residue was converted into the (E)-2-butenedioate salt in ethanol. The salt was filtered off and dried, yielding 4.3 parts (50%) of 2-amino-N-[2-[4-[[9-[(4-fluorophenyl)methyl]-9H-purin-8-yl]amino]-1-piperidinyl]ethyl]benzamide (E)-2-butenedioate(2:5); mp. 164° C. (compound 178).

Example 46

A mixture of 0.7 parts of isothiocyanatomethane, 3.7 parts of N-[1-(2-aminoethyl)-4-piperidinyl]-9-[(4-fluorophenyl)methyl]-9H-purin-8-amine and 90 parts of tetrahydrofuran was stirred for 4 hours at room temperature. After evaporation, the residue was purified by column chromatography over silica gel using a mixture of trichloromethane and methanol, saturated with ammonia, (95:5 by volume) as eluent. The first fraction was collected and the eluent was evaporated. The residue was crystallized from acetonitrile. The product was filtered off and dried, yielding 1.3 parts (29%) of N-[2-[4-[[9-[(4-fluorophenyl)methyl]-9H-purin-8-yl]amino]-1-piperidinyl]ethyl]-N'-methylthiourea; mp. 205.5° C. (compound 179).

In a similar manner there is also prepared:

N-[2-[4-[[9-[(4-fluorophenyl)methyl]-9H-purin-8-yl]methyl]-1-piperidinyl]ethyl]-N'-ethylurea; (compound 180).

Example 47

To a stirred and cooled (−10° C.) mixture of 5.6 parts of N,N'-methanetetraylbis[cyclohexanamine], 13.9 parts of carbon disulfide and 90 parts of tetrahydrofuran were added portionwise 10 parts of N-[1-(2-aminoethyl)-4-piperidinyl]-9-[(4-fluorophenyl)methyl]-9H-purin-8-amine. Upon completion, the temperature was allowed to rise to room temperature and the reaction mixture was evaporated, yielding 16 parts of 9-[(4-fluorophenyl)methyl]-N-[1-(2-isothiocyanatoethyl)-4-piperidinyl]-9H-purin-8-amine (compound 181).

A mixture of 2.95 parts of 3,4-pyridinediamine, 16 parts of 9-[(4-fluorophenyl)methyl]-N-[1-(2-isothiocyanatoethyl)-4-piperidinyl]-9H-purin-8-amine, and 90 parts of tetrahydrofuran was stirred and refluxed overnight. The reaction mixture was evaporated. The residue was purified by column chromatography over silica gel using a mixture of trichloromethane and methanol, saturated with ammonia, (95/5 by volume) as eluent. The pure fractions were collected and the eluent was evaporated, yielding 10.5 parts of N-(4-amino-3-pyridinyl)-N'-[2-[4-[[9-[(4-fluorophenyl)methyl]-9H-purin-8-yl]-amino]-1-amino]-1-piperidinyl]ethyl]thiourea (compound 182).

A mixture of 10.5 parts of N-(4-amino-3-pyridinyl)-N'-[2-[4-[[9-[(4-fluorophenyl)methyl]-9H-purin-8-yl]-amino]-1-piperidinyl]-ethyl]thiourea, 6 parts of mercury(II) oxide, 1 part of sulfur and 120 parts of ethanol was stirred and refluxed overnight. The reaction mixture was filtered over Hyflo ® while hot. The filtrate was evaporated. The residue was purified by column chromatography over silica gel using a mixture of trichloromethane and methanol, saturated with ammonia, (90:10 by volume) as eluent. The pure fractions were collected and the eluent was evaporated. The residue was converted into the (E)-2-butenedioate salt in ethanole. The salt was filtered off and dried, yielding 4 parts (17%) of 9-[(4-fluorophenyl)methyl]-N-[1-[2-[(1H-imidazo[4,5-c]pyridin-2-yl)amino]ethyl]-4-piperidinyl]-9H-purin-8-amine (E)-2-butenedioate(1:3) monohydrate; mp. 191.0° C. (compound 183).

Example 48

To a previously prepared sodium methoxide solution, starting from 25 parts of sodium in 400 parts of methanol, were added 49.4 parts of 6-chloro-9-[(4-fluorophenyl)methyl]-8-[[1-(phenylmethyl)-4-piperidinyl]methyl]-9H-purine. After stirring for 8 hours at reflux temperature, the reaction mixture was cooled and 1000 parts of water were added. The precipitated product was filtered off and dried, yielding 34.5 parts (70.4%) of 9-[(4-fluorophenyl)methyl]-6-methoxy-8-[[1-(phenylmethyl)-4-piperidinyl]methyl]-9H-purine (compound 184).

Example 49

A mixture of 3 parts of 6-chloro-9-[(4-fluorophenyl)methyl]-8-[[1-(phenylmethyl)-4-piperidinyl]-methyl]-9H-purine and 50 parts of a hydrochloric acid solution 1N was stirred and refluxed for 1.5 hours. After cooling, the mixture was made alkaline with ammonium hydroxide. The product was extracted with trichloromethane. The extract was washed with water, dried, filtered and evaporated. The residue was crystallized from a mixture of acetonitrile and ethanol. The product was filtered off and dried, yielding 1.5 parts (52%) of 9-[(4-fluorophenyl)methyl]-1,9-dihydro-8-[[1-(phenylmethyl)-4-piperidinyl]methyl]-6H-purin-6-one; mp. 197.0° C. (compound 185).

Example 50

A mixture of 2.7 parts of 9-[(4-fluorophenyl)methyl]-8-[[1-[2-(4-methoxyphenyl)ethyl]-4-piperidinyl]-methyl]-9H-purin-6-ol and 75 parts of a hydrobromic acid solution 48% in water was stirred for 4 hours at 80° C. After evaporation, the residue was taken up in water and treated with sodium carbonate. The product was extracted with trichloromethane. The extract was dried, filtered and evaporated. The residue was purified by column chromatography over silica gel using a mixture of trichloromethane and methanol, saturated with ammonia, (90:10 by volume) as eluent. The pure fractions were collected and the eluent was evaporated. The residue was crystallized from ethanol and acetonitrile. The product was filtered off and dried, yielding 1 part (38.6%) of 9-[(4-fluorophenyl)methyl]-8-[[1-[2-(4-hydroxyphenyl)ethyl]-4-piperidinyl]-methyl]-9H-purin-6-ol; mp. 215.7° C. (compound 186).

In a similar manner there was also prepared:

4-[[4-[[7-[(4-fluorophenyl)methyl]-7H-purin-8-yl]amino]-1-piperidinyl]methyl]phenol; mp. 228.1° C. (compound 187).

In a similar manner there is also prepared:

2-[2-[4-[[9-[(4-fluorophenyl)methyl]-9H-purin-8-yl]methyl]-1-piperidinyl]ethyl]phenol (compound 188).

Example 51

To a stirred solution of 7.2 parts of 4-[[9-[(4-fluorophenyl)methyl]-9H-purin-8-yl]thio]-1-[(4-methylphenyl)sulfonyl]piperidine in 195 parts of dichloromethane is added dropwise a solution of 7 parts of 3-chlorobenzenecarboperoxoic acid in 65 parts of dichloromethane. Upon completion, stirring is continued for 2 hours at room temperature. The whole is washed with a sodium carbonate solution and twice with water, dried, filtered and evaporated. The residue is crystallized from acetonitrile. The product is filtered off and dried, yielding 3 parts (40%) of 4-[[9-[(4-fluorophenyl)-methyl]-9H-purin-8-yl]sulfonyl]-1-[(4-methylphenyl)-sulfonyl]piperidine; (compound 189).

C. Pharmacological Examples

The useful antihistaminic properties of the compounds of formula (I) are demonstrated in the following test procedure.

Example 52

Protection of Rats from Compound 48/80-Induced Lethality

Compound 48/80, a mixture of oligomers obtained by condensation of 4-methoxy-N-methylbenzeneethanamine and formaldehyde has been described as a potent histamine releasing agent (Int. Arch. Allergy. 13, 336 (1958)). The protection from compound 48/80-induced lethal circulatory collapse appears to be a simple way of evaluating quantitatively the antihistaminic activity of test compounds. Male rats of an inbred Wistar strain, weighing 240–260 g were used in the experiment. After overnight starvation the rats were transferred to conditioned laboratories (temp.=21±1° C. relative humidity =65±5%). The rats were treated subcutaneously or orally with a test compound or with the solvent (NaCl solution, 0.9%). One hour after treatment there was injected intravenously compound 48/80, freshly dissolved in water, at a dose of 0.5 mg/kg (0.2 ml/100 g of body weight). In control experiments, wherein 250 solvent-treated animals were injected with the standard dose of compound 48/80, not more than 2.8% of the animals survived after 4 hours. Survival after 4 hours is therefore considered to be a safe criterion of a protective effect of drug administration.

The $ED_{50}$-values of the compounds of formula (1) are listed in Table 1. Said $ED_{50}$-values are the values in mg/kg body weight at which the tested compounds protect 50% of the tested animals against compound 48/80-induced lethality.

TABLE 1

| Compound No. | compound 48/80 lethality test in rats-$ED_{50}$ in mg/kg body weight |
|---|---|
| 60 | 0.08 |
| 61 | 0.01 |
| 62 | 0.04 |
| 64 | 0.08 |
| 74 | 0.01 |
| 75 | 0.08 |
| 76 | 0.02 |
| 77 | 0.02 |
| 78 | 0.04 |
| 79 | 0.04 |
| 80 | 0.04 |
| 81 | 0.04 |
| 83 | 0.08 |
| 87 | 0.08 |
| 88 | 0.02 |
| 89 | 0.08 |
| 100 | 0.02 |
| 104 | 0.04 |
| 106 | 0.08 |
| 107 | 0.02 |
| 114 | 0.04 |
| 115 | 0.08 |
| 141 | 0.01 |
| 142 | 0.02 |
| 143 | 0.02 |
| 144 | 0.04 |
| 145 | 0.01 |
| 165 | 0.02 |
| 167 | 0.08 |
| 168 | 0.02 |
| 169 | 0.08 |
| 171 | 0.08 |
| 172 | 0.04 |
| 173 | 0.08 |
| 183 | 0.04 |

D) Composition Examples

The following formulations exemplify typical pharmaceutical compositions in dosage unit form suitable for systemic administration to animal and human subjects in accordance with the instant invention.

"Active ingredient" (A.I.) as used throughout these examples relates to a compound of formula (I) or a pharmaceutically acceptable acid addition salt thereof.

Example 53: Oral Drops

500 Grams of the A.I. was dissolved in 0.5 liters of 2-hydroxy-propanoic acid and 1.5 liters of the polyethylene glycol at 60°~80° C. After cooling to 30°~40° C. there were added 35 liters of polyethylene glycol and the mixture was stirred well. Then there was added a solution of 1750 grams of sodium saccharin in 2.5 liters of purified water and while stirring there were added 2.5 liters of cocoa flavor and polyethylene glycol q.s. to a volume of 50 liters, providing an oral drop solution comprising 10 milligrams of the A.I. per milliliter. The resulting solution was filled into suitable containers.

Example 54: Oral Solution

9 Grams of methyl 4-hydroxybenzoate and 1 gram of propyl 4-hydroxybenzoate were dissolved in 4 liters of boiling purified water. In 3 liters of this solution were dissolved first 10 grams of 2,3-dihydroxybutanedioic acid and thereafter 20 grams of the A.I. The latter solution was combined with the remaining part of the former solution and 12 liters 1,2,3-propanetriol and 3 liters of sorbitol 70% solution were added thereto. 40 Grams of sodium saccharin were dissolved in 0.5 liters of water and 2 milliliters of raspberry and 2 milliliters of gooseberry essence were added. The latter solution was combined with the former, water was added q.s. to a volume of 20 liters providing an oral solution comprising 20 milligrams of the active ingredient per teaspoonful (5 milliliters). The resulting solution was filled in suitable containers.

Example 55: Capsules

20 Grams of the A.I., 6 grams sodium lauryl sulfate, 56 grams starch, 56 grams lactose, 0.8 grams colloidal silicon dioxide, and 1.2 grams magnesium stearate were vigorously stirred together. The resulting mixture was subsequently filled into 1000 suitable hardened gelating capsules, comprising each 20 milligrams of the active ingredient.

Example 56: Film-Coated Tablets

Preparation of Tablet Core

A mixture of 100 grams of the A.I., 570 grams lactose and 200 grams starch was mixed well and thereafter humidified with a solution of 5 grams sodium dodecyl sulfate and 10 grams polyvinylpyrrolidone (Kollidon-K 90 ®) in about 200 milliliters of water. The wet powder mixture was sieved, dried and sieved again. Then there was added 100 grams microcrystalline cellulose (Avicel ®) and 15 grams hydrogenated vegetable oil (Sterotex ®). The whole was mixed well and compressed into tablets, giving 10.000 tablets, each containing 10 milligrams of the active ingredient.

Coating

To a solution of 10 grams methyl cellulose (Methocel 60 HG ®) in 75 milliliters of denaturated ethanol there was added a solution of 5 grams of ethyl cellulose (Ethocel 22 cps ®) in 150 milliliters of dichloromethane. Then there were added 75 milliliters of dichloromethane and 2.5 milliliters 1,2,3-propanetriol. 10 Grams of polyethylene glycol was molten and dissolved in 75 milliliters of dichloromethane. The latter solution was added to the former and then there were added 2.5 grams of magnesium octadecanoate, 5 grams of polyvinylpyrrolidone and 30 milliliters of concentrated colour suspension (Opaspray K-1-2109 ®) and the whole was homogenated. The tablet cores were coated with the thus obtained mixture in a coating apparatus.

Example 57: Injectable Solution 1.8 Grams methyl 4-hydroxybenzoate and 0.2 grams propyl 4-hydroxybenzoate were dissolved in about 0.5 liters of boiling water for injection. After cooling to about 50° C. there were added while stirring 4 grams lactic acid, 0.05 grams propylene glycol and 4 grams of the A.I.

The solution was cooled to room temperature and supplemented with water for injection q.s. ad 1 liter volume, giving a solution of 4 milligrams A.I. per milliliters. The solution was sterilized by filtration (U.S.P. XVII p. 811) and filled in sterile containers.

Example 58: Suppositories

3 Grams A.I. was dissolved in a solution of 3 grams 2,3-dihydroxybutanedioic acid in 25 milliliters polyethylene glycol 400. 12 Grams surfactant (SPAN ®) and triglycerides (Witepsol 555 ®) q.s. ad 300 grams were molten together. The latter mixture was mixed well with the former solution. The thus obtained mixture was poured into moulds at a temperature of 37°~38° C. to form 100 suppositories each containing 30 milligrams of the active ingredient.

What we claim is:
1. A compound of the formula:

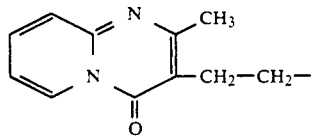

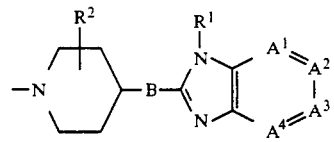

a pharmaceutically acceptable acid addition salt or a possible stereochemically isomeric form thereof, wherein:
—A¹=A²—A³=A⁴— represents a bivalent radical of the formula:

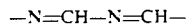

or $$-CH=N-CH=N-$$ (a-2), wherein one or two hydrogen atoms in said radicals (a-1) or (a-2) may, each independently from each other, be replaced by halo, $C_{1-6}$alkyl, $C_{1-6}$alkyloxy, trifluoromethyl, or hydroxy;

$R^1$ represents $C_{1-6}$alkyl substituted with one $Ar^1$ radical;

$R^2$ represents a member selected from the group consisting of hydrogen and $C_{1-6}$alkyl; and B represents NH, wherein in the foregoing:

$Ar^1$ represents a member selected from the group consisting of phenyl, substituted phenyl, naphthalenyl, thienyl, halothienyl, $C_{1-6}$alkylthienyl, pyridinyl, mono- and di($C_{1-6}$alkyloxy)pyridinyl, pyrrolyl, $C_{1-6}$alkylpyrrolyl, furanyl, furanyl substituted with $C_{1-6}$alkyl, pyrazinyl, thiazolyl, imidazolyl, $C_{1-6}$alkylimidazolyl; said substituted phenyl being phenyl substituted with up to 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, $C_{1-6}$alkylsulfonyl, $C_{1-6}$alkylsulfonyl$C_{1-6}$alkyl, phenyl$C_{1-6}$alkylsulfonyl, phenylsulfonyl$C_{1-6}$alkyl, a radical of the formula $R^8-C_pH_{2p}-Y-$, a radical of the formula $R^9-Z-C(=X)-Y-$, and a radical of the formula $R^{10}SO_2Y-$; wherein $R^8$ represents a member selected from the group consisting of amino, cyano, phenylaminocarbonyl, mono- and di($C_{1-6}$alkyl)aminocarbonyl, $C_{1-6}$alkyloxycarbonyl, phenyl$C_{1-6}$alkyloxycarbonyl, 4-morpholinylcarbonyl, 1-piperidinylcarbonyl, 1-pyrrolidinylcarbonyl, and $C_{2-6}$alkenyl; wherein p represents an integer of from 1 to 6 inclusive; wherein Y represents O, S, $NR^3$, or a direct bond; wherein Z represents O, S, $NR^5$, or a direct bond; wherein $R^9$ represents a member selected from the group consisting of hydrogen, $C_{1-6}$alkyl, and $Ar^2$, provided that when $R^9$ is hydrogen and Y is other than a direct bond, then Z is not O or S; wherein X is as defined above; and wherein $R^{10}$ represents $C_{1-6}$alkyl or $Ar^2$; and $Ar^2$ represents a member selected from the group consisting of phenyl, substituted phenyl, thienyl, and furanyl, said substituted phenyl being phenyl substituted with up to three substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl.

2. The compound of claim 1 wherein:
$R^1$ is 2-pyrazinyl-methylene, 2-furanyl-methylene, 2-thienyl-methylene, 2-pyridinyl-methylene, 5-methyl-2-furanyl-methylene, 4-fluorobenzyl, benzyl, or 4-thiazolyl-methylene;
$R^2$ is hydrogen or methyl; and
—A¹=A²—A³=A⁴— is —N=CH—N=CH—, —CH=N—CH=N—, —C(OH)=N—CH=N— or —N=CH—N=C(CH₃)—.

3. An anti-allergic composition comprising a suitable pharmaceutical carrier and as the active ingredient an anti-allergic effective amount of a compound of the formula:

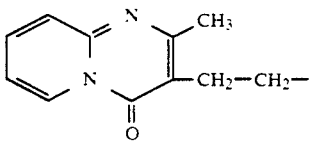

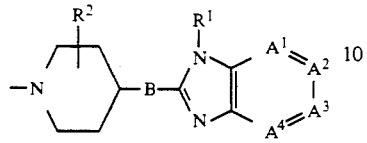

a pharmaceutically acceptable acid addition salt or a possible stereochemically isomeric form thereof, wherein:

—$A^1$=$A^2$—$A^3$=$A^4$— represents a bivalent radical of the formula:

     (a-1);

or

     (a-2), wherein one or two hydrogen atoms in said radicals (a-1) or (a-2) may, each independently from each other, be replaced by halo, $C_{1-6}$alkyl, $C_{1-6}$alkyloxy, trifluoromethyl, or hydroxy;

$R^1$ represents $C_{1-6}$alkyl substituted with one $Ar^1$ radical;

$R^2$ represents a member selected from the group consisting of hydrogen and $C_{1-6}$alkyl; and B represents NH, wherein in the foregoing:

$Ar^1$ represents a member selected from the group consisting of phenyl, substituted phenyl, naphthalenyl, thienyl, halothienyl, $C_{1-6}$alkylthienyl, pyridinyl, mono- and di($C_{1-6}$alkyloxy)pyridinyl, pyrrolyl, $C_{1-6}$alkylpyrrolyl, furanyl, furanyl substituted with $C_{1-6}$alkyl, pyrazinyl, thiazolyl, imidazolyl, $C_{1-6}$alkylimidazolyl; said substituted phenyl being phenyl substituted with up to 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, $C_{1-6}$alkylsulfonyl, $C_{1-6}$alkylsulfonyl$C_{1-6}$alkyl, phenyl$C_{1-6}$alkylsulfonyl, phenylsulfonyl$C_{1-6}$alkyl, a radical of the formula $R^8$—$C_pH_{2p}$—Y—, a radical of the formula $R^9$—Z—C(=X)—Y—, and a radical of the formula $R^{10}SO_2Y$—; wherein $R^8$ represents a member selected from the group consisting of amino, cyano, phenylaminocarbonyl, mono- and di($C_{1-6}$alkyl)aminocarbonyl, $C_{1-6}$alkyloxycarbonyl, phenyl$C_{1-6}$alkyloxycarbonyl, 4-morpholinylcarbonyl, 1-piperidinylcarbonyl, 1-pyrrolidinylcarbonyl, and $C_{2-6}$alkenyl; wherein p represents an integer of from 1 to 6 inclusive; wherein Y represents O, S, $NR^3$, or a direct bond; wherein Z represents O, S, $NR^5$, or a direct bond; wherein $R^9$ represents a member selected from the group consisting of hydrogen, $C_{1-6}$alkyl, and $Ar^2$, provided that when $R^9$ is hydrogen and Y is other than a direct bond, then Z is not O or S; wherein X is as defined above; and wherein $R^{10}$ represents $C_{1-6}$alkyl or $Ar^2$; and $Ar^2$ represents a member selected from the group consisting of phenyl, substituted phenyl, thienyl, and furanyl, said substituted phenyl being phenyl substituted with up to three substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl.

4. The anti-allergic composition of claim 3 wherein:

$R^1$ is 2-pyrazinyl-methylene, 2-furanyl-methylene, 2-thienyl-methylene, 2-pyridinyl-methylene, 5-methyl-2-furanyl-methylene, 4-fluorobenzyl, benzyl, or 4-thiazolyl-methylene;

$R^2$ is hydrogen or methyl; and

—$A^1$=$A^2$—$A^3$=$A^4$— is —N=CH—N=CH—, —CH=N—CH=N—, —C(OH)=N—CH=N— or —N=CH—N=C(CH_3)—.

5. A method of treating allergic diseases in warm-blooded animals suffering from same, which method comprises the systemic administration to warm-blooded animals of an effective anti-allergic amount of a compound of the formula:

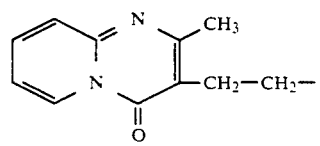

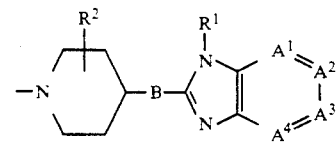

a pharmaceutically acceptable acid addition salt or a possible stereochemically isomeric form thereof, wherein:

—$A^1$=$A^2$—$A^3$=$A^4$— represents a bivalent radical of the formula:

     (a-1);

or

     (a-2), wherein one or two hydrogen atoms in said radicals (a-1) or (a-2) may, each independently from each other, be replaced by halo, $C_{1-6}$alkyl, $C_{1-6}$alkyloxy, trifluoromethyl, or hydroxy;

$R^1$ represents $C_{1-6}$alkyl substituted with one $Ar^1$ radical;

$R^2$ represents a member selected from the group consisting of hydrogen and $C_{1-6}$alkyl; and B represents NH, wherein in the foregoing:

$Ar^1$ represents a member selected from the group consisting of phenyl, substituted phenyl, naphthalenyl, thienyl, halothienyl, $C_{1-6}$alkylthienyl, pyridinyl, mono- and di($C_{1-6}$alkyloxy)pyridinyl, pyrrolyl, $C_{1-6}$alkylpyrrolyl, furanyl, furanyl substituted with $C_{1-6}$alkyl, pyrazinyl, thiazolyl, imidazolyl, $C_{1-6}$alkylimidazolyl; said substituted phenyl being phenyl substituted with up to 3 substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, $C_{1-6}$alkylsulfonyl, $C_{1-6}$alkylsulfonyl$C_{1-6}$alkyl, phenyl$C_{1-6}$alkylsulfonyl, phenylsulfonyl$C_{1-6}$alkyl, a radical of the formula $R^8-C_pH_{2p}-Y-$, a radical of the formula $R^9-Z-C(=X)-Y-$, and a radical of the formula $R^{10}SO_2Y-$; wherein $R^8$ represents a member selected from the group consisting of amino, cyano, phenylamino-carbonyl, mono- and di($C_{1-6}$alkyl)aminocarbonyl, $C_{1-6}$alkyloxycarbonyl, phenyl$C_{1-6}$alkyloxycarbonyl, 4-morpholinylcarbonyl, 1-piperidinylcarbonyl, 1-pyrrolidinylcarbonyl, and $C_{2-6}$alkenyl; wherein p represents an integer of from 1 to 6 inclusive; wherein Y represents O, S, $NR^3$, or a direct bond; wherein Z represents O, S, $NR^5$, or a direct bond; wherein $R^9$ represents a member selected from the group consisting of hydrogen, $C_{1-6}$alkyl, and $Ar^2$, provided that when $R^9$ is hydrogen and Y is other than a direct bond, then Z is not O or S; wherein X is as defined above; and wherein $R^{10}$ represents $C_{1-6}$alkyl or $Ar^2$; and $Ar^2$ represents a member selected from the group consisting of phenyl, substituted phenyl, thienyl, and furanyl, said substituted phenyl being phenyl substituted with up to three substituents each independently selected from the group consisting of halo, hydroxy, nitro, cyano, trifluoromethyl, $C_{1-6}$alkyl, $C_{1-6}$alkyloxy, $C_{1-6}$alkylthio, mercapto, amino, mono- and di($C_{1-6}$alkyl)amino, carboxyl, $C_{1-6}$alkyloxycarbonyl, and $C_{1-6}$alkylcarbonyl.

6. The method of claim 5 wherein:

$R^1$ is 2-pyrazinyl-methylene, 2-furanyl-methylene, 2-thienyl-methylene, 2-pyridinyl-methylene, 5-methyl-2-furanyl-methylene, 4-fluorobenzyl, benzyl, or 4-thiazolyl-methylene;

$R^2$ is hydrogen or methyl; and $-A^1=A^2-A^3=A^4-$ is $-N=CH-N=CH-$, $-CH=N-CH=N-$, $-C(OH)=N-CH=N-$ or $-N=CH-N=C(CH_3)-$.

* * * * *